(12) United States Patent
Yonetoku et al.

(10) Patent No.: US 7,557,112 B2
(45) Date of Patent: Jul. 7, 2009

(54) AROMATIC-RING-FUSED PYRIMIDINE DERIVATIVE

(75) Inventors: Yasuhiro Yonetoku, Tokyo (JP); Kenji Negoro, Tokyo (JP); Kenichi Onda, Tokyo (JP); Masahiko Hayakawa, Tokyo (JP); Daisuke Sasuga, Tokyo (JP); Takahiro Nigawara, Tokyo (JP); Kazuhiko Iikubo, Tokyo (JP); Hiroyuki Moritomo, Tokyo (JP); Shigeru Yoshida, Tokyo (JP); Takahide Ohishi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/576,889

(22) PCT Filed: Oct. 5, 2005

(86) PCT No.: PCT/JP2005/018412

§ 371 (c)(1),
(2), (4) Date: Apr. 9, 2007

(87) PCT Pub. No.: WO2006/040966

PCT Pub. Date: Apr. 20, 2006

(65) Prior Publication Data

US 2007/0249587 A1    Oct. 25, 2007

(30) Foreign Application Priority Data

Oct. 8, 2004    (JP) ............................. 2004-295559

(51) Int. Cl.
| A61P 3/10 | (2006.01) |
| C07D 495/04 | (2006.01) |
| C07D 279/12 | (2006.01) |
| C07D 417/04 | (2006.01) |
| C07D 413/04 | (2006.01) |
| A61K 31/541 | (2006.01) |
| A61K 31/5355 | (2006.01) |
| A61K 31/519 | (2006.01) |

(52) U.S. Cl. ...................... 514/260.1; 544/278; 544/61; 544/117; 544/58.4; 544/255; 544/279; 540/600; 540/575; 514/217.06; 514/218; 514/228.5; 514/234.2

(58) Field of Classification Search ............... 514/260.1, 514/217.06, 218; 544/278, 584, 61, 117, 544/228.5, 234.2, 255; 540/576, 600
See application file for complete search history.

(56) References Cited

U.S. PATENT DOCUMENTS

| 4,146,716 A * | 3/1979 | Cox et al. ................... 544/278 |
| 4,196,207 A * | 4/1980 | Webber .................... 514/260.1 |
| 4,871,739 A | 10/1989 | Baldwin et al. |
| 7,223,766 B2 * | 5/2007 | Dugar et al. .............. 514/258.1 |
| 2003/0199526 A1 | 10/2003 | Choquette et al. |
| 2004/0038856 A1 | 2/2004 | Chakravarty et al. |
| 2004/0138238 A1 | 7/2004 | Dhanoa et al. |
| 2005/0004143 A1 | 1/2005 | Dugar et al. |
| 2005/0096333 A1 | 5/2005 | Dugar et al. |
| 2006/0229306 A1 | 10/2006 | Terricabras Belart et al. |

FOREIGN PATENT DOCUMENTS

| CA | 1308410 | 10/1992 |
| CA | 2 469 316 A1 | 6/2003 |
| EP | 0 276 057 | 7/1988 |
| EP | 1 277 738 A1 | 1/2003 |
| GB | 1 597 786 | 9/1981 |
| JP | 63-192778 | 8/1988 |
| JP | 6-220059 | 8/1994 |
| JP | 2005-120102 | 5/2005 |
| WO | WO 03/049739 A1 | 6/2003 |
| WO | WO/2004/014850 | * 2/2004 |
| WO | WO/2004/087056 | * 10/2004 |
| WO | WO 2004/087056 A2 | 10/2004 |
| WO | WO/2005/014558 | * 2/2005 |
| WO | WO 2005/032481 | 4/2005 |

OTHER PUBLICATIONS

Tibaldi, Expert Rev. Endocrin. & Metab., vol. 3, No. 2, Mar. 2008, pp. 147-159(13).*
Langvin, New Eng. J. Med., vol. 345, No. 24, Dec. 13, 2001, 1772-1774.*
Succurro, et al., Obesity (2008) doi:10.1038/oby.2008.308 (Abstract).*
Kuroda, et al., Biol. Pharm. Bull. 28(5) 937-939 2005).*
"The Effect of Intensive Treatment of Diabetes on the Development and Progression of Long-Term Complications in Insulin-Dependent Diabetes Mellitus", The New England Journal of Medicine, vol. 329, No. 14, Sep. 30, 1993, pp. 1-23.

(Continued)

*Primary Examiner*—Mark L Berch
*Assistant Examiner*—Cecilia M Jaisle
(74) *Attorney, Agent, or Firm*—Oblon, Spivak, McClelland, Maier & Neustadt, P.C.

(57) ABSTRACT

There are provided novel pyrimidine derivatives which has been fused with an aromatic heterocycle selected from thiophene, thiazole and pyridine or pharmaceutically acceptable salts thereof; and a pharmaceutical composition comprising said compound as an active ingredient. These compounds exhibit excellent promoting activity on insulin secretion and activity against hyperglycemia. Hence, the pharmaceutical compositions comprising such compounds as active ingredients, based on these actions, are useful for treating and/or preventing insulin-dependent diabetes (type 1 diabetes), non-insulin-dependent diabetes (type 2 diabetes), insulin-resistant diseases, obesity, and the like.

22 Claims, No Drawings

OTHER PUBLICATIONS

"Glucose Tolerance and Mortality: Comparison of Who and American Diabetic Association Diagnostic Criteria", The Lancet, vol. 354, Aug. 21, 1999, pp. 617-621.

Irene M. Stratton, et al. "Association of Glycaemia With Macrovascular and Microvascular Complications of Type 2 Diabetes (UKPDS 35): Prospective Observational Study", British Medical Journal, vol. 321, Aug. 12, 2000, pp. 405-413.

J. Bourguignon, et al. "Syntheses de Thieno [2,3-d] Pyrimidines Substituees en 2 et 4", Bullitin de la Societe Chimique de France, No. 3-4, 1975, pp. 815-819.

J.P. Osselaere, et al. "Derives des Amino-4 Aryl-2 Pyrido[2,3-d] Pyrimidines Doues de Proprietes Anti-Inflammatoires et Spasmolytiques", Annales Pharmaceutiques Francaises, vol. 32, No. 11, 1974, pp. 575-579.

* cited by examiner

AROMATIC-RING-FUSED PYRIMIDINE DERIVATIVE

TECHNICAL FIELD

The present invention relates to novel aromatic ring fused pyrimidine derivatives or pharmaceutically acceptable salts thereof useful as drugs, particularly as insulin secretagogues or diabetic therapeutic agents, and to a drug comprising these compounds as active ingredients.

BACKGROUND ART

Diabetes is a disease with chronic hyperglycemia as a cardinal sign and develops by absolute or relative deficiency of insulin activity. Clinically, diabetes is roughly classified by the characteristic into insulin-dependent diabetes (referred to as "Type 1 diabetes" hereinafter) and non-insulin-dependent diabetes (referred to as "Type 2 diabetes" hereinafter). In Type 2 diabetes, which accounts for approximately 90% of diabetic patients, decrease of insulin secretion from the pancreatic β-cells is one of major causes of the onset, and postprandial hyperglycemia caused by early disorder in insulin secretion is particularly recognized. Presently, sulfonylurea drug (SD drug) is the mainstream as the insulin secretagogue, but it is likely to cause hypoglycemia and known to cause secondary ineffectiveness due to pancreatic exhaustion following long-term administration. Moreover, SU drug is effective to control blood glucose between meals, but has difficulty in suppressing postprandial hyperglycemia. Recent large-scale clinical trials have confirmed that remedying postprandial hyperglycemia is critical in controlling diabetic complications and diabetic development (non-patent document 1). It is also reported that arteriosclerosis develops only during periods of the postprandial hyperglycemia and that the persistence of minor postprandial hyperglycemia increases mortality caused by cardiovascular disease or the like. (non-patent document 2 and 3). This indicates that postprandial hyperglycemia is, even at minor levels, an independent risk factor of cardiovascular death. From the above background, attention has been paid to importance and necessity for medications against postprandial hyperglycemia. Hence, drugs having promoting activity on insulin secretion are considered to have an appropriate profile to remedy postprandial hyperglycemia and/or fasting blood glucose and to be useful for treating and preventing of Type 1 and Type 2 diabetes.

WO 2004/065391 pamphlet (patent document 1) discloses thiophene-fused pyrimidine derivatives substituted with a cyano group as phosphodiesterase 7 (PDE 7) inhibitors and describes Type 1 and Type 2 diabetes as examples of diseases that are expected to be improved by inhibition of PDE 7. However, neither compounds of the present invention are specifically disclosed, nor are specific data indicating their applicability to diabetes therapy such as promoting activity on insulin secretion.

In WO 03/049739 pamphlet (patent document 2) discloses fused pyrimidine derivatives as glycogen synthase kinase-3 (GSK-3) inhibitors and describes diabetes as an example of diseases for which these compounds are useful, that is, diseases caused by action of GSK-3. However, none of compounds of the present invention are specifically disclosed therein, and there are not disclosed specific data indicating their applicability of said compounds to diabetes therapy such as promoting activity on insulin secretion, either.

WO 2005/032481 pamphlet (patent document 3) discloses fused pyrimidine derivatives as Transforming growth factor-beta (TGFβ) inhibitors, but does not specifically disclose the compounds of the present invention. Neither description nor suggestion is given on applicability of said compounds to diabetes therapy including promotion of insulin secretion, either.

WO 2004/087056 pamphlet (patent document 4) discloses fused pyrimidine derivatives as Transforming growth factor-beta (TGFβ) inhibitors, but does not specifically disclose the compounds of the present invention. Neither description nor suggestion is given on applicability of said compounds to diabetes therapy including promotion of insulin secretion, either.

WO 03/097615 pamphlet (patent document 5) discloses fused pyrimidine derivatives as Transforming growth factor-beta (TGFβ) inhibitors but does not specifically disclose the compounds of the present invention. Neither description nor suggestion is given on applicability of said compounds to diabetes therapy including promotion of insulin secretion, either.

WO 2004/014850 pamphlet (patent document 6) discloses 5-membered aromatic heterocycle fused pyrimidine derivatives as neurokinin antagonists, but does not specifically disclose the compounds of the present invention. Neither description nor suggestion is given on applicability of said compounds to diabetes therapy including promotion of insulin secretion, either.

US Patent Publication U.S. Pat. No. 4,196,207 (patent document 7) discloses thiophene-fused pyrimidine derivatives as miticides, but does not specifically disclose the compounds of the present invention. Neither description nor suggestion is given on applicability of said compounds to diabetes therapy including promotion of insulin secretion, either.

US Patent Publication U.S. Pat. No. 4,146,716 (patent document 8) discloses thiophene-fused pyrimidine derivatives as antifungal agents, antiviral agents and pesticides, but does not specifically disclose the compounds of the present invention. Neither description nor suggestion is given on applicability of said compounds to diabetes therapy including promotion of insulin secretion, either.

Furthermore, thiephene-fused pyrimidine derivatives and pyridine-fused pyrimidine derivatives are disclosed in the literature relating to synthetic organic chemistry (non-patent document 4 and 5).

non-patent document 1: N. Engl. J. Med., 329: 977-986, 1993
non-patent document 2: Lancet, 354: 617, 1999
non-patent document 3: Brit. Med. J., 321: 405-413, 2000
non-patent document 4. Bulletin de la Societe Chimique de France, 3-4(PT.2), 815-819, 1975
non-patent document 5: Annales Pharmaceutiques Francaises, 32(11), 575-579, 1974
patent document 1: WO 2004/065391
patent document 2: WO 03/049739
patent document 3: WO 2005/032481
patent document 4: WO 2004/087056
patent document 5: WO 03/097615
patent document 6: WO 2004/014850
patent document 7: U.S. Pat. No. 4,196,207
patent document 8: U.S. Pat. No. 4,146,716

DISCLOSURE OF THE INVENTION

Problems to be Solved by the Invention

As described above, since insulin secretagogues are useful for treating and preventing Type 1 diabetes, Type 2 diabetes and insulin-resistant diseases, creation of further superior insulin secretagogues is earnestly desired.

Means for Solving the Problems

The present inventors earnestly studied compounds with promoting activity on insulin secretion, found that the aromatic ring fused pyrimidine derivatives of the present invention have excellent effects of promoting insulin secretion, and completed the present invention.

That is, the present invention provides fused pyrimidine derivatives represented by formula (I) or pharmaceutically acceptable salts thereof, and a pharmaceutical composition containing these compounds as active ingredients and a pharmaceutical composition serving as a therapeutic agent for Type 1 diabetes, Type 2 diabetes and/or insulin-resistant diseases.

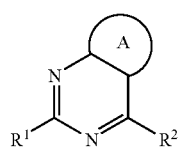

(I)

[symbols in the formula represent the following meaning;
A:
A ring selected from the group consisting of Group $X^1$ and Group $X^2$, furthermore, the carbon atoms which form the structure of this ring may be substituted with one or more group(s) selected from the group consisting of lower alkyl, —O-lower alkyl, halogen, carboxyl, —$CO_2$-lower alkyl and carbamoyl.

Group $X^1$:
A group selected from the group consisting of

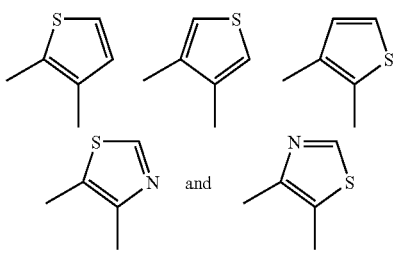

Group $X^2$:
A group selected from the group consisting of

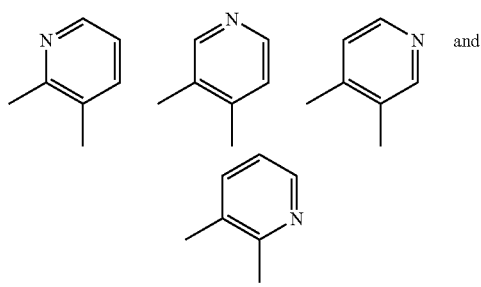

—$R^1$: A phenyl substituted with at least one halogen. Additionally, this phenyl may have more substituent. However, when A is a ring selected from Group $X^2$, —$R^1$ indicates a phenyl substituted with at least three halogens.
—$R^2$:
A group represented by Formula (II) or optionally substituted cycloamino;

(II)

[symbols in the formula represent the following meaning;
—$R^{21}$, —$R^{22}$:
A group selected from the group consisting of the identical or different —H, lower alkyl, lower alkenyl, lower alkynyl-cycloalkyl, phenyl-aromatic heterocycle, non-aromatic heterocycle and —O-lower alkyl. Additionally, each of these groups may have substituent.]

However, when A is a ring selected from Group $X^1$, —$R^2$ indicates optionally substituted cycloamino.]

Furthermore, it is preferable that A in Formula (I) is a ring selected from Group $X^1$.

Additionally, it is preferable that $R^1$ in Formula (I) is phenyl substituted with at least one halogen; and more preferably, is phenyl substituted with at least three halogens.

Additionally, it is preferable that $R^2$ in formula (I) is optionally substituted cycloamino and more preferably, is optionally substituted piperazino or optionally substituted piperidino.

Furthermore, preferably the fused pyrimidine derivative represented by Formula (I) is the compound in which A is a ring selected from Group $X^1$; and more preferably is the compound in which A is a ring selected from Group $X^1$ and $R^1$ is phenyl substituted with at least three halogens; and much more preferably, is the compound in which A is a ring selected from Group $X^1$, $R^1$ is phenyl substituted with at least three halogens and $R^2$ is optionally substituted cycloamino; and most preferably, is the compound in which A is a ring selected from Group $X^1$, $R^1$ is a phenyl substituted with at least three halogens and $R^2$ is optionally substituted piperazino or optionally substituted piperidino.

Effects of the Invention

The compound of the present invention have excellent activities in promoting insulin secretion and suppressing increase in blood glucose. Hence, the compounds of the present invention represented by Formula (I), based on said activities, are effective to treat and/or prevent Type 1 diabetes, Type 2 diabetes, and/or insulin-resistant diseases.

Pharmacological action of the compounds of the present invention was confirmed by the following test examples.

(1) Assay for Promoting Activity on Insulin Secretion

In this assay, promoting activities on insulin secretion of the test compounds were studied using MIN6B1 cell, which was a strain of mouse pancreatic β-cells, and glibenclamide, which was a commercially available insulin secretagogue, as a reference compound. The assay procedure is given below.

MIN6B1 cells were seeded on a 48-well plate at a concentration of $1 \times 10^5$ cells/well (0.25 ml) (The medium was prepared by adding FCS (fetal calf serum) to DMEM (Dulbecco's Modified Eagle Medium) containing 25 mM glucose such that the FCS concentration became 10%). After two days, the medium was suctioned by an aspirator, each well washed four times with 0.2 ml of KRE-HEPES buffer [Kregs-Ringer-bicarbonate-N-2-hydroxyethylpiperazine-N'-2-ethanesulfonic acid; 130 mM NaCl, 4.7 mM KCl, 1.2 mM $KH_2PO_4$, 1.2 mM $MgCl_2.6H_2O$, 0.25 mM $CaCl_2.2H_2O$, 2.5 mM $NaHCO_3$, 0.5% BSA, and 10 mM N-2-hydroxyethylpiperazine-N'-2-ethanesulfonic acid (pH 7.4)] containing 2.8 mM glucose warmed to 37° C., 0.2 ml of said buffer was again added, and the cells were incubated at 37° C. for 30 to 60 minutes. After the buffer was suctioned by an aspirator, 0.25 mL of a solution containing 10 μM of each test compound in KRB-HEPES containing 16.8 mM glucose was added to each well, and the cells were incubated at 37° C. for 22 minutes. The samples were pipetted and diluted by 25 to 51 times, and the insulin concentrations were analyzed using an insulin assay kit (Rat Insulin [$^{125}$I] Biotrak Assay System with Magnetic Separation; Amersham BioScience K.K.). The subject compound was dissolved in 100% DMSO and was added at a final concentration of 0.1%. The activity was expressed relatively when the DMSO was considered to be 100%. The results are shown in Table 1.

TABLE 1

| Test Compound | Promotion activity on insulin secretion, % |
|---|---|
| Example 134 | 284 |
| Example 345 | 249 |
| Example 361 | 162 |
| Glibenclamide | 122 |

As shown above, the compounds that are active ingredients of the drug of the present invention and the compounds of the present invention exhibited higher promoting activities on insulin secretion than glibenclamide, a commercially available insulin secretagogue.

(2) Oral Glucose Tolerance Test on Normal Mouse

In this assay, preventive activities of test compounds against hyperglycemia following glucose loading were examined using normal mice and nateglinide, a commercially available oral anti-hyperglycemic agent, as a reference compound. The assay procedure is given below.

ICR mice (male, 6 weeks old) that had been preliminary bred for one week were fasted for 18 to 20 hours to use as test animals. Each test compound was dissolved in 0.5% methylcellulose solution and orally administered at 3 mg/kg (10 mg/kg for nateglinide) before glucose loading. Timing to administer the test compound was selected to be optimal for each test compound, which was 10 minutes before glucose loading for the compounds of the present invention or 30 minutes before glucose loading for nateglinide, which was a reference compound. The hypoglycemic rate (%) at 30 minutes after glucose loading was measured relative to the control group. The results are shown in Table 2.

TABLE 2

| Test compound | Hypoglycemic rate, % |
|---|---|
| Example 99 | 36 |
| Example 104 | 34 |
| Example 329 | 36 |
| Nateglinide | 26 |

As shown above, the compounds that were active ingredients of the drug of the present invention and the compounds of the present invention exhibited more potent preventive action against hyperglycemia after glucose loading even at a lower dose than nateglinide, a commercially available oral hypoglycemic drug.

BEST MODE FOR CARRYING OUT THE INVENTION

The compounds of the present invention are further described as follows.

In the present description, the term "lower" means straight or branched carbon chain having 1 to 6 carbon(s) unless otherwise noted. Therefore, "lower alkyl" means straight chain or branched $C_1$-$C_6$ alkyl and its specific examples are methyl, ethyl, propyl, isopropyl, butyl, isobutyl, sec-butyl, tert-butyl, pentyl, neopentyl and hexyl, etc. Preferably, it is $C_1$-$C_3$ alkyl; methyl, ethyl, propyl and isopropyl. "lower alkenyl" means straight chain or branched $C_2$-$C_6$ alkenyl and its specific examples are vinyl, allyl and butenyl, etc. "lower alkynyl" means straight chain or branched $C_2$-$C_6$ alkynyl and its specific examples are propargyl, etc. "lower alkylidene" means straight chain or branched $C_1$-$C_6$ alkylidene and its specific examples are methylidene, ethylidene and propylidene, etc.

"Halogen" means fluoro, chloro, bromo or iodo, and preferably, means fluoro, chloro or bromo.

"Cycloamino" means a monovalent group derived from 3 to 8-membered non-aromatic cyclic amine that contains at least one nitrogen atom and optionally contains one or more identical or different additional heteroatom(s) selected from the group consisting of nitrogen, oxygen and sulfur, wherein the nitrogen atom necessarily present in said ring is the bonding site. Furthermore, the sulfur atom(s) on the said cycloamino ring may be oxidized. And Specific examples are univalent groups such as azetidine, pyrrolidine, piperidine, azepane, azocane, piperazine, homopiperazine, morpholine, oxazepane, thiomorpholine and thioazepane, etc. Additionally, this ring also may have unsaturated bonds on part of the ring such as dihydropyrrole, tetrahydropyridine, tetrahydroazepine, imidazolidine, oxazolidine, dihydrooxazine, thiazolidene and dihydrothiazine, etc. Furthermore, this ring may fuse with cycloalkyl such as decahydroquinoline and decahydroisoquinoline, etc. Additionally, this ring may fuse with phenyl such as indoline, 1,2,3,4-tetrahydroquinoline and 1,2,3,4-tetrahydroisoquinoline, etc. And this ring may also fuse with other cycloamino such as octahydroimidazo[1,5-a]pyrazine and octahydro[1,2-a]pyrazine, etc. And this ring may also fuse with aromatic heterocycle such as 2,3,4,9-tetrahydro-1H-b-carboline, 4,5,6,7-tetrahydro-1H-pyrazolo[4,3-c]pyridine, 4,5,6,7-tetrahydro-2H-pyrazolo[4,3-c]pyridine and 5,6,7,8-tetrahydropyrido[4,3-d]pyrimidine, etc. Additionally, this ring may have spiro-fuse with non-aromatic heterocycle such as 1,3,8-triazaspiro[4.5]decane, 1-oxa-8-azaspiro[4.5]decane, 1,4-dioxa-8-azaspiro[4.5]decane, 2.4-dioxa-9-azaspiro[5.5]undecane and 2,8-diazaspiro[4.5]decane, etc. And this cyclic amino may also be bridged, as monovalent groups derived from 2,5-diazabicyclo[2.2.1]heptane, 2,5-diazabicyclo[2.2.2]octane, and others.

"Cycloalkyl" means 3 to 8-membered carbon ring and some of the carbons may have unsaturated bonds. Specific examples are cyclopropyl, cyclopentyl, cyclohexyl, cyclooctyl, cyclobutenyl, cyclohexenyl and cyclooctadienyl, etc. This ring may also fuse with phenyl.

"Aromatic heterocycle" means a monovalent group derived from 5 to 6-membered aromatic heterocycle containing one or more identical or different heteroatom(s) selected from the group consisting of nitrogen, oxygen and sulfur.

Specific examples are univalent groups such as pyrrole, pyridine, pyrazole, imidazole, pyridazine, pyrimidine, pyrazine, triazol, triazine, tetrazole, furan, thiophene, oxazole, thiazole, oxadiazole and thiadiazole, etc. Furthermore, this ring may fuse with phenyl ring such as indole, indazole and quinoline, etc. and may be partially hydrogenated such as tetrahydropyridine, tetrahydroazepine, dihydropyridine and indoline, etc.

"Non-aromatic heterocycle" means a monovalent group derived from 5 to 6 membered saturated heterocycle containing one or more identical or different heteroatom(s) selected from the group consisting of nitrogen, oxygen and optionally oxidized sulfur. Specific examples are, in addition to the above-mentioned cycloamino, monovalent groups in which an atom other than the nitrogen atom in the above cyclic amino is the bonding site, and monovalent groups such as tetrahydrofuran, tetrahydropyran, tetrahydrothiofuran, tetrahydrothiopyran, dioxolane, 1,3-dioxane and 1.4-dioxane, etc. And this ring may be bridged such as 1-azabicyclo[2.2.1] heptane and quinuclidine, etc.

Furthermore, "bridged cycloamino" means a monovalent group in which two non-adjacent carbon atoms that make up the ring of the above-mentioned cycloamino are bridged by methylene, ethylene or trimethylene.

For substituents that are acceptable by the word "substituted" and "may have substituent" in the present specification, any substituent commonly found as substituent on said group may be present. Furthermore, one or more of these substituents may be present on each group.

For acceptable substituents in "a phenyl substituted with at least one halogen" in "a phenyl substituted with at least one halogen. Additionally, this phenyl may have more substituent" of $R^1$, in "a cycloamino which may have substituent" of $R^2$ and in substituted "cycloalkyl, phenyl, aromatic heterocycle, non-aromatic heterocycle" of $R^{21}$ and $R^{22}$, the groups of (a) to (h) given below are cited as examples. Furthermore, [$R^Z$] indicates lower alkyl which may be substituted with one or more group(s) selected from the group consisting of —OH, —O-lower alkyl, —OCO-lower alkyl, carboxyl, —$CO_2$-lower alkyl, —CO-lower alkyl, carbamoyl which may be substituted with one or two lower alkyl(s), cyano, amino which may be substituted with one or two lower alkyl(s), phenyl, aromatic heterocycle, cycloalkyl, non-aromatic heterocycle and halogen.

(a) Halogen;
(b) —OH, —O—$R^Z$, —O-phenyl, —OCO—$R^Z$, —OCONH—$R^Z$, oxo(=O);
(c) —SH, —S—$R^Z$, —S-phenyl, —S-aromatic heterocycle, —SO—$R^Z$, —SO-phenyl, —SO-aromatic heterocycle, —$SO_3$H, —$SO_2$—$R^Z$, —$SO_2$-phenyl (this phenyl may be substituted with lower alkyl), —$SO_2$-aromatic heterocycle (this aromatic heterocycle may be substituted with lower alkyl), sulfamoyl which may be substituted with one or two $R^Z$;
(d) amino which may be substituted with one or two $R^Z$, —NHCO—$R^Z$, —NHCO-phenyl, —$NHCO_2$—$R^Z$, —$NHCONH_2$, —NHCONH—$R^Z$, —$NHSO_2$—$R^Z$, —$NHSO_2$-phenyl (this phenyl may be substituted with lower alkyl), —$NHSO_2NH_2$, nitro;
(e) —CHO, —CO—$R^Z$, —$CO_2$H, —$CO_2$—$R^Z$, carbamoyl which may be substituted with one or two $R^Z$, —CO-cycloamino (this cycloamino may be substituted with —OH or oxo), —COCO—$R^Z$, cyano;
(f) phenyl or cycloalkyl, each of which may be substituted with one or more group(s) selected from the group consisting of —OH, —O-lower alkyl, oxo, —S-lower alkyl, amino which may be substituted with one or two lower alkyl(s), cycloamino, —$CO_2$H, carbamoyl which may be substituted with one or two $R^Z$, halogen and $R^Z$;
(g) aromatic heterocycle or non-aromatic heterocycle, each of which may be substituted with one or more group(s) selected from the group consisting of —OH, —O-lower alkyl, oxo, —S-lower alkyl, amino which may be substituted with one or two lower alkyl(s), cycloamino, —$CO_2$H, carbamoyl that may be substituted with one or two $R^Z$, halogen and $R^Z$;
(h) lower alkyl, lower alkenyl or lower alkylidene, each of which may be substituted with one or more group(s) selected from the above mentioned substituents described in (a) to (g).

Additionally, for acceptable substituents in "lower alkyl, lower, alkenyl, lower alkynyl and —O-lower alkyl" which may have substituent of $R^{21}$ and $R^{22}$, the above mentioned groups described in (a) to (g) are cited as examples.

The compounds of the present invention represented by formula (I) may have (an) asymmetric carbon atom(s) depending on the substituents and optical isomers may exist based on this fact. The present invention encompasses all of mixtures and isolated compounds of these optical isomers. The compounds of the present invention may exist in a form of tautomers. Any separated tautomers and mixtures thereof are included in the present invention. The present invention also encompasses labeled species, that is, compounds in which one or more atoms in the compounds of the present invention are replaced by a radioactive isotope or non-radioactive isotope.

The compounds of the present invention may form a salt, which is encompassed in the present invention so far as such salt is pharmaceutically acceptable. Said salts specifically include salts with an inorganic acid such as hydrochloric acid, hydrobromic acid, hydroiodic acid, sulfuric acid, nitric acid, and phosphoric acid; salts with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, p-toluenesulfonic acid, aspartic acid, and glutamic acid; salts with an inorganic base containing a metal such as sodium, potassium, calcium, and magnesium; salts with an organic base such as methylamine, ethylamine, ethanolamine, lysine, and ornithine; ammonium salt, and others. Furthermore, the present invention encompasses various hydrates, solvates, and all crystal polymorphs of the compounds of the present invention and pharmaceutically acceptable salts thereof. The present invention encompasses all of so-called prodrugs, that is, compounds that are metabolized in vivo to be converted into the compounds represented by formula (I) or salts thereof. As groups used for forming the prodrugs of the present invention, there may be mentioned groups described in Prog Med., 5, 2157-2161 (1985) and in "Development of Drugs," Vol. 7 "Molecular Design," pp. 163-198, Hirokawa Shoten (1990).

The compounds of the present invention and pharmaceutically acceptable salts thereof can be manufactured by applying various known synthetic methods utilizing characteristics based on the skeletal structure thereof or type of substituents. Typical preparation methods are illustrated below. They can be also manufactured according to the description in Reference Examples and Examples described hereinafter or by similar methods thereto. Depending on properties of functional groups, it is sometimes advantageous in manufacturing techniques that said functional group is replaced with an appropriate protective group, that is, group readily convertible to said functional group, in a stage of starting material or intermediate. The protective group is thereafter removed as needed to obtain desired compounds. Such functional groups include hydroxyl, carboxyl, amino, and others. Protective groups therefor include, for example, groups described in Greene and Wuts, "Protective Groups in Organic Synthesis (third edition)", which may be used as appropriate according to reaction conditions to be employed.

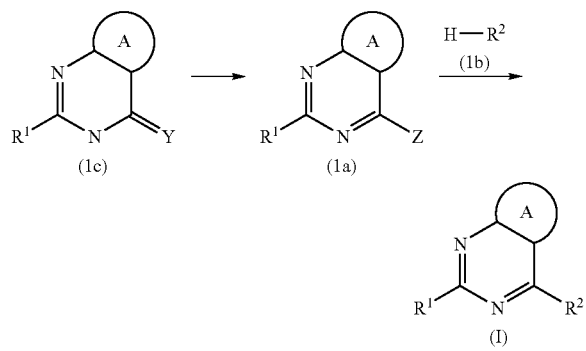

(In the scheme, ring A, $R^1$ and $R^2$ represent the same meaning as the above. Y represents O or S, and Z represents a leaving group. Ditto hereinafter.)

The present preparation method is a method in which an aromatic ring-condensed pyrimidine derivative having a leaving group represented by formula (1a) is reacted with an amine derivative represented by formula (1b) to manufacture the compound of the present invention represented by general formula (I).

The leaving group represented by Z in compound (1a) means a group that can be eliminated together with the hydrogen atom of the amino group in compound (1b) in a form of HZ under the reaction condition. Examples thereof include halogen atoms such as fluoro, chloro, bromo, and iodo, lower alkylsulfonyloxy groups such as methanesulfonyloxy, trihalomethanesulfonyloxy groups such as trifluoromethanesulfonyloxy, arylsulfonyloxy groups such as benzenesulfonyloxy and p-toluenesulfonyloxy, and others.

The reaction of compound (1a) with compound (1b) is conducted under normal or positive pressure in the absence of solvent or in an appropriate solvent.

Specific examples of the solvent include aromatic hydrocarbons such as toluene and xylene; ketones such as methyl ethyl ketone and methyl isobutyl ketone; ethers such as ether, tetrahydrofuran (THF) dioxane, and diglyme; alcohols such as methanol (MeOH), ethanol (EtOH), and 2-propanol (iPrOH); acetonitrile, dimethylformamide (DEM), 1,3-dimethyl-2-imidazolidinone (DMI), dimethylsulfoxide (DMSOC, water, and mixtures thereof. The present reaction is preferably performed in the presence of a base, which specifically includes alkali carbonates such as sodium carbonate and potassium carbonate, alkali hydrogencarbonates such as sodium hydrogencarbonate and potassium hydrogencarbonate; tertiary amines such as triethylamine and diisopropylethylamine; and others. Excess amount of compound (1b) may be used to function as a base. The reaction temperature is generally about 20° C. to about 180° C., and preferably about 60° C. to about 130° C., depending on the starting compounds, reaction conditions and others.

Compound (1a) can be synthesized, for example, by or sulfonylating a pyrimidinone or pyrimidinethione derivative represented by formula (1c) according to common procedures.

Halogenation in the present reaction is carried out, for example, by reacting compound (1c) with a halogenating agent such as phosphorous oxychloride and phosphorous tribromide. Sulfonylation is carried out, for example, by reacting compound (1c) in which Y is an oxygen atom with a sulfonylating agent such as methanesulfonyl chloride, p-toluenesulfonyl chloride, trifluoromethanesulfonyl chloride, and trifluoromethanesulfonic anhydride.

Compound (1c) can be synthesized by a known method, for example, the methods described in J. Am. Chem. Soc., 74, 842 (1952), Chem. Ber., 95, 937 (1962), or J. Org. Chem., 29, 2887 (1964) or similar methods thereto. Compound (1b) is commercially available or can be synthesized by a known method.

Some compounds of the present invention can be manufactured from another compound of the present invention manufactured by the above preparation method, methods described in Examples, methods obvious to those skilled in the art, or variation thereof, through procedures generally used by those skilled in the art such as alkylation, acylation, substitution reaction, oxidation, reduction, and hydrolysis, which are publicly known.

The compounds of the present invention thus manufactured are purified for isolation as a free form or a salt after converting to a salt by known treatment. Isolation and purification are performed using common chemical operations such as extraction, concentration, evaporation, crystallization, filtration, recrystallization, and various chromatographic techniques.

When the compound of the present invention has an asymmetric carbon, there are optical isomers. Such optical isomers can be resolved by a common method such as fractional crystallization, in which an appropriate salt is recrystallized, and column chromatography. Optically active compounds can be also manufactured using appropriate optically active starting materials.

The drugs of the present invention can be prepared by a common method using one or more compounds of the present invention and carriers for drugs, excipients, or other additives commonly used in preparation. Administration may be in either form of oral administration of tablets, pills, capsules, granules, powder, liquids, or the like, or parenteral administration of injections such as intravenous injection and intramuscular injection or suppositories, transnasal, transmucosal, or percutaneous administration, or the like.

Solid compositions used for oral administration in the present invention include tablets, powder, granules, and others. In such solid compositions, one or more active substances are mixed with at least one inert diluent such as lactose, manitol, glucose, hydroxypropylcellulose, microcrystalline cellulose, starch, polyvinylpyrrolidone, and magnesium aluminometasilicate. Such compositions may contain, according to a common method, additives other than inert diluents, for example, lubricants such as magnesium stearate, disintegrating agents such as calcium cellulose glycolate, stabilizers, solubilizing agents, and others. Tablets or pills may be coated as needed with sugar coating or gastric soluble or enteric film such as sucrose, gelatin, hydroxypropylcellulose, and hydroxypropylmethylcellulose phthalate.

Liquid compositions for oral administration include pharmaceutically acceptable emulsion, liquid, suspension, syrup, elixir, and others. The composition contains a common inert diluent, for example, purified water or ethanol (EtOH). Such composition may contain, besides inert diluents, adjuvants such as wetting agents and suspending agents, sweeteners, flavor, fragrances, and preservatives.

Injections for parenteral administration contain sterile aqueous or non-aqueous solvent, suspension medium, or emulsifying medium. Aqueous solvent or suspension medium includes, for example, distilled water for injection and physiological saline. Non-aqueous solvent or suspension medium includes, for example, propylene glycol, polyethylene glycol, vegetable oils such as olive oil, alcohols such as EtOH and polysorbate 80 (Pharmacopoeia name), and others. Such compositions may further contain adjuvants such as preservatives, wetting agents, emulsifiers, dispersants, stabilizers, and solubilizing agents. These are sterilized, for example, by passing through a sterile bacteria filter, formulating with a bactericide, or radiation. These may be also used after manufacturing a sterile solid composition, which is dissolved in sterile water or a sterile solvent for injection prior to use.

The proper dose per day in oral administration is generally about 0.0001 to 50 mg/kg of body weight, preferably about 0.001 to 10 mg/kg, and more preferably 0.01 to 1 mg/kg, which is administered once or dividedly into two to four times. The proper dose per day in intravenous administration is about 0.0001 to 1 mg/kg of body weight, and preferably about 0.001 to 0.1 mg/kg, which is administered once per day or dividedly into multiple times per day. The dose is properly determined in accordance with each case considering symptom age, sex, and others.

EXAMPLES

The present invention is specifically described in accordance with Examples hereinafter, but not limited in any way by these Examples. Some starting compounds used in Examples are new substances and methods for manufacturing them from known substances are described as Reference Examples.

Reference Example 1

After stirring a mixture of 4-chloro-2,5-difluorobenzoic acid, thionyl chloride and DMF at 70° C. for one hour and additionally at 80° C. for 1.5 hours, the solvent was removed under reduced pressure and THF was added. This reaction solution was added to a mixture of methyl 3-aminothiophene-2-carboxylate, THF and diisopropylethylamine in an MeOH-ice bath and stirred at room temperature for 1.5 days to give methyl 3-[(4-chloro-2,5-difluorobenzoyl)amino]thiophene-2-carboxylate.

The compounds shown in Table 3 below were manufactured according to a similar manner to that of Reference Example 1. Furthermore, the symbols in the Table indicate the following (same as below).
Rf: Reference Example number
Data: Spectral data (MS: FAB-MS(M+H)$^+$; MN: FAB-MS (M−H)$^-$; MM: FAB-MS(M)$^+$)
Structure: Chemical Structure Formula
R, R$^A$, R$^B$: Substituent groups in the general formula structure (Me: methyl, Et: ethyl, nPr: n-propyl, iPr: isopropyl, nBu: n-butyl, cPr: cyclopropyl, cPen: cyclopentyl cHex: cyclohexyl, cHep: cycloheptyl cOct: cyclooctyl, pyrr: pyrrolidine-1-yl, pipe: piperidine-1-yl, mor: morpholine-4-yl, tmor: thiomorpholine-4-yl, pipa: piperazine-1-yl, azep: azepane-1-yl, hpipa: homopiperazine-1-yl, hPy: 1,2,3,6-tetrahydropyridine-1-yl, Py: pyridyl, fur: furyl, imid: 1H-imidazole-1-yl, tet: tetrazole-5-yl, Pyox: 1-oxidopyridyl, Pyone: 2-oxo-1,2-dihydropyridyl, Ph: phenyl, Br: benzyl, Ac: acetyl, Boc: tert-butyloxycarbonyl, Ms: methanesulfonyl, MOM: methoxymethyl, di: di, tri: tri.

Figure(s) before a substituent show(s) substituted position(s), and for example, 5-Br-2-fur means 5-bromofuran-2-yl).

TABLE 3

| Rf | Structure | Data |
|---|---|---|
| 1 | (4-F, 5-Cl, 2-F benzoyl)-NH-thiophen-3-yl-2-CO₂Me | MS: 332 |
| 1-1 | (2,4,5-triF benzoyl)-NH-thiophen-3-yl-2-CO₂Me | |
| 1-2 | (4-Cl, 2,5-diF benzoyl)-NH-(4-Me-thiophen-3-yl)-2-CO₂Me | MS: 346 |
| 1-3 | (4-Cl, 2,5-diF benzoyl)-NH-pyridin-3-yl-4-CO₂Me | MS: 327 |
| 1-4 | (2,4,5-triF benzoyl)-NH-(4-Me-thiophen-3-yl)-2-CO₂Me | |
| 1-5 | (4-Cl, 2,5-diF benzoyl)-NH-pyridin-2-yl-3-CO₂Me | MS: 327 |
| 1-6 | (4-Cl, 2,5-diF benzoyl)-NH-thiophen-3-yl-4-CO₂Me | MS: 332 |
| 1-7 | (4-Br, 2,5-diF benzoyl)-NH-(4-Me-thiophen-3-yl)-2-CO₂Me | |

TABLE 3-continued

| Rf | Structure | Data |
|---|---|---|
| 1-8 | (4-chloro-2,5-difluoro-N-(3-methoxycarbonylpyridin-4-yl)benzamide structure) | MS: 327 |

Reference Example 2

A mixture of methyl 3-[(4-chloro-2,5-difluorobenzoyl)amino]thiophene-2-carboxylate, MeOH, THF and 1M sodium hydroxide (NaOH) solution (aq) was stirred for two hours at 85° C. to give 3-[(4-chloro-2,5-difluorobenzoyl)amino]thiophene-2-carboxylic acid.

The compounds shown in Table 4 below were manufactured according to a similar manner to that of Reference Example 2.

TABLE 4

| Rf | Structure | Data |
|---|---|---|
| 2 | (4-chloro-2,5-difluorobenzoyl thiophene-2-carboxylic acid) | MS: 318 |
| 2-1 | (2,4,5-trifluorobenzoyl thiophene-2-carboxylic acid) | MS: 302 |
| 2-2 | (4-chloro-2,5-difluorobenzoyl 4-methylthiophene-2-carboxylic acid) | MS: 332 |
| 2-3 | (2,4,5-trifluorobenzoyl 4-methylthiophene-2-carboxylic acid) | MS: 316 |
| 2-4 | (4-chloro-2,5-difluorobenzoyl thiophen-3-yl carboxylic acid) | MN: 316 |
| 2-5 | (4-bromo-2,5-difluorobenzoyl 4-methylthiophene-2-carboxylic acid) | MS: 377 |
| 2-6 | (4-fluorobenzoyl thiophene-2-carboxylic acid) | MS: 266 |
| 2-7 | (4-chlorobenzoyl thiophene-2-carboxylic acid) | MN: 280 |
| 2-8 | (4-bromobenzoyl thiophene-2-carboxylic acid) | MN: 325 |

Reference Example 3

After a mixture of methyl 4-methyl-3-[(2,4,5-trifluorobenzoyl)amino]thiophene-2-carboxylate, MeOH, THF and 1M NaOH aq was stirred at 70° C., 1M of hydrochloric acid aq was added and the extracted solid was filtered to give 3-[(2,5-difluoro-4-methoxybenzoyl)amino]-4-methythiophene-2-carboxylic acid.

MS: 328

Reference Example 4

After a mixture of 3-[(4-chloro-2,5-difluorobenzoyl)amino]thiophene-2-carboxylic acid, thionyl chloride and DMF was stirred for 1.5 hours at 75° C., the solvent was removed under reduced pressure and 1,4-dioxane was added. After the reaction solution was added to 28% ammonia water under ice cooling and stirred at room temperature for 3 hours, the solvent was removed under reduced pressure. MeOH and 1M NaOH aq were added to the obtained residue and stirred for 2.5 hours at 90° C. to give 2-(4-chloro-2,5-difluorophenyl)thieno[3,2-d]pyrimidine-4(1H)-one.

The compounds shown in Table 5 below were manufactured according to a similar manner to that of Reference Example 4.

TABLE 5

| Rf | Structure | Data |
|---|---|---|
| 4 | (2-(4-chloro-2,5-difluorophenyl)thieno[3,2-d]pyrimidin-4(3H)-one) | MS: 299 |
| 4-1 | (2-(2,4,5-trifluorophenyl)thieno[3,2-d]pyrimidin-4(3H)-one) | MS: 283 |
| 4-2 | (2-(4-chloro-2,5-difluorophenyl)-7-methylthieno[3,2-d]pyrimidin-4(3H)-one) | MS: 297 |
| 4-3 | (7-methyl-2-(2,4,5-trifluorophenyl)thieno[3,2-d]pyrimidin-4(3H)-one) | MS: 297 |
| 4-4 | (2-(4-chloro-2,5-difluorophenyl)thieno[2,3-d]pyrimidin-4(3H)-one) | MS: 299 |
| 4-5 | (2-(4-bromo-2,5-difluorophenyl)-7-methylthieno[3,2-d]pyrimidin-4(3H)-one) | — |

TABLE 5-continued

| Rf | Structure | Data |
|---|---|---|
| 4-6 | (2-(4-fluorophenyl)thieno[3,2-d]pyrimidin-4(3H)-one) | MS: 247 |
| 4-7 | (2-(4-chlorophenyl)thieno[3,2-d]pyrimidin-4(3H)-one) | MS: 263 |
| 4-8 | (2-(4-bromophenyl)thieno[3,2-d]pyrimidin-4(3H)-one) | MS: 307, 309 |

Reference Example 5

28% ammonia water was added to a chloroform-MeOH solution of methyl 2-[(4-chloro-2,5-difluorobenzoyl)amino] nicotinate and the resultant was stirred all night at room temperature to give 2-(4-chloro-2,5-difluorophenyl)pyrido [2,3-d]pyrimidine-4(3H)-one.

The compounds shown in Table 6 below were manufactured according to a similar manner to that of Reference Example 5.

TABLE 6

| Rf | Structure | Data |
|---|---|---|
| 5 | (2-(4-chloro-2,5-difluorophenyl)pyrido[2,3-d]pyrimidin-4(3H)-one) | MS: 294 |
| 5-1 | (2-(4-chloro-2,5-difluorophenyl)pyrido[3,4-d]pyrimidin-4(3H)-one) | MS: 294 |

TABLE 6-continued

| Rf | Structure | Data |
|---|---|---|
| 5-2 | (pyrido-pyrimidinone with 5-chloro-2-fluoro-...-fluoro-phenyl) | MS: 294 |

Reference Example 6 n-butyllithium was added to a diethyl ether solution of 1-bromo-4-chloro-5-fluoro-2-(methoxymethoxy)benzene in a dry ice-acetone bath and stirred for one hour. The reaction solution was added to a mixture of dry ice and diethyl ether and stirred for two hours to give lithium 4-chloro-5-fluoro-2-(methoxymethoxy)benzoate. Phosphorus oxychloride was added to a mixture of the obtained lithium 4-chloro-5-fluoro-2-(methoxymethoxy)benzoate, 3-aminothiophene-2-carboxamide and pyridine in a MeOH ice bath and stirred for one hour to give 3-{[4-chloro-5-fluoro-2-(methoxymethoxy)benzoyl]amino}thiophene-2-carboxamide.

ES-MS(M+Na): 381

Reference Example 7

After stirring a mixture of 4-bromo-2,5-difluorobenzoic acid and thionyl chloride for one hour at 80° C., the solution was removed and an oily substance was obtained. A mixture of the obtained oily substance, 3-aminothiophene-2-carboxamide, N,N-diisopropylethylamine and THF was stirred for two hours under ice cooling to give 3-[(4-bromo-2,5-difluorobenzoyl)amino]thiophene-2-carboxamide.

The compounds shown in Table 7 below were manufactured according to a similar manner to that of Reference Example 7.

TABLE 7

| Rf | Structure | Data |
|---|---|---|
| 7 | 4-bromo-2,5-difluorobenzoyl-aminothiophene-2-carboxamide | EI-MS(+): 219, 221 |
| 7-1 | 3,4,5-trifluorobenzoyl-aminothiophene-2-carboxamide | MS: 301 |
| 7-2 | 2,4,6-trifluorobenzoyl-aminothiophene-2-carboxamide | MS: 301 |
| 7-3 | 4-fluorobenzoyl-aminothiophene-2-carboxamide | |
| 7-4 | 4-chloro-3-fluorobenzoyl-aminothiophene-2-carboxamide | FAB-MS (M + Na): 321 |
| 7-5 | 4-chloro-2,5-difluorobenzoyl-aminothiazole-4-carboxamide | MS: 318 |
| 7-6 | 4-bromo-3,5-difluorobenzoyl-aminothiophene-2-carboxamide | MN: 360 |
| 7-7 | 4-bromobenzoyl-aminothiophene-2-carboxamide | |
| 7-8 | 2,6-difluorobenzoyl-aminothiophene-2-carboxamide | MS: 283 |
| 7-9 | 4-bromobenzoyl-aminothiophene-3-carboxamide | MS: 325, 327 |

TABLE 7-continued

| Rf | Structure | Data |
|---|---|---|
| 7-10 | 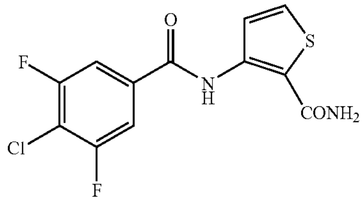 | MN: 315 |
| 7-11 | 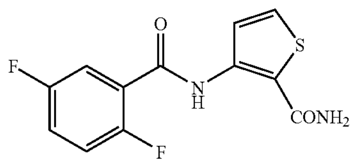 | FAB-MS (M + Na): 305 |
| 7-12 | 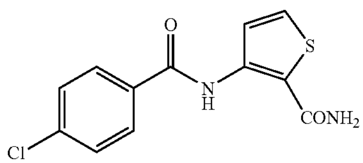 | |
| 7-13 | 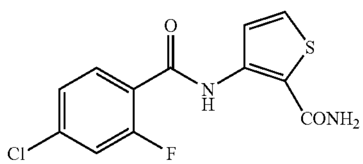 | MS: 299 |

Reference Example 8

A mixture of 3-[(4-bromo-2,5-difluorobenzoyl)amino]thiophene-2-carboxamide; 1M NaOH aq and MeOH was stirred for two hours at 80° C. to give 2-(4-bromo-2,5-difluorophenyl)thieno[3,2-d]pyrimidine-4(1H)-one.

The compounds shown in Table 8 below were manufactured according to a similar manner to that of Reference Example 8.

TABLE 8

| Rf | Structure | Data |
|---|---|---|
| 8 | 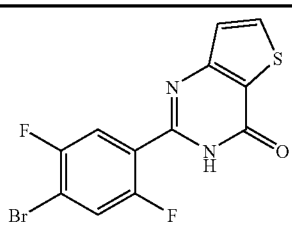 | EI-MS(+): 343, 345 |
| 8-1 | 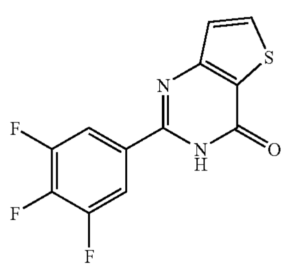 | MS: 283 |

TABLE 8-continued

| Rf | Structure | Data |
|---|---|---|
| 8-2 | 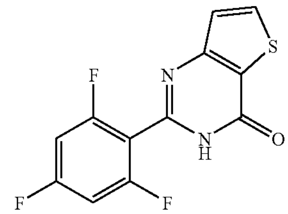 | MS: 283 |
| 8-3 | 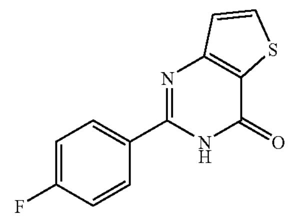 | MS: 247 |
| 8-4 | 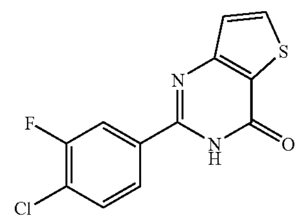 | MS: 281 |
| 8-5 | 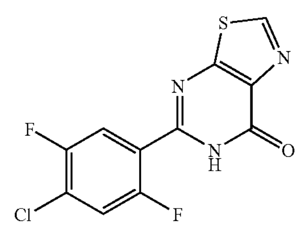 | MS: 298 |
| 8-6 | 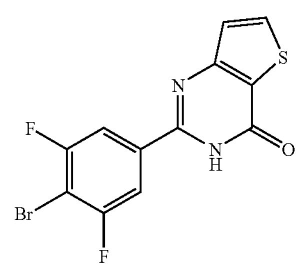 | ES-MS(+): 343 |
| 8-7 | 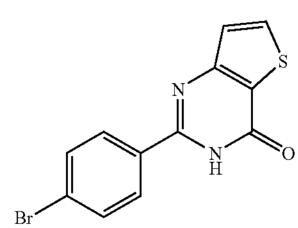 | MS: 307, 309 |

TABLE 8-continued

| Rf | Structure | Data |
|---|---|---|
| 8-8 | (2,6-difluorophenyl thieno[3,2-d]pyrimidin-4(3H)-one) | MS: 265 |
| 8-9 | (2-(4-bromophenyl) thieno[3,2-d]pyrimidin-4(3H)-one) | MS: 307, 309 |
| 8-10 | (2-(4-chloro-3,5-difluorophenyl) thieno[3,2-d]pyrimidin-4(3H)-one) | MS: 299 |
| 8-11 | (2-(2,5-difluorophenyl) thieno[3,2-d]pyrimidin-4(3H)-one) | MS: 265 |
| 8-12 | (2-(4-chlorophenyl) thieno[3,2-d]pyrimidin-4(3H)-one) | MS: 263 |
| 8-13 | (2-(4-chloro-2-fluorophenyl) thieno[3,2-d]pyrimidin-4(3H)-one) | MS: 281 |

Reference Example 9

3-aminothiophene-2-carboxamide was added to an acetic acid solution of 4,5-dichlorophthalic anhydride and stirred all night heated to reflux to give 3-(5,6-dichloro-1,3-dioxo-1,3-dihydro-2H-isoindole-2-yl)thiophene-2-carboxamide. 1M NaOH aq was added to THF-MeOH solution of the obtained 3-(5,6-dichloro-1,3-dioxo-1,3-dihydro-2H-isoindole-2-yl) thiophene-2-carboxamide and stirred for 2.5 hours at 80° C. to give 4,5-dichloro-2-(4-oxo-3,4-dihydrothieno[3,2-d]pyrimidine-2-yl)benzoic acid. Sulfuric acid was added to a MeOH-1,4-dioxane solution of the obtained 4,5-dichloro-2-(4-oxo-3,4-dihydrothieno[3,2-d]pyrimidine-2-yl)benzoic acid and stirred for three days at 70° C. to give methyl 4,5-dichloro-2-(4-oxo-3,4-dihydrothieno[3,2-d]pyrimidine-2-yl)benzoate.

MS: 355

Reference Example 10

A mixture of 2-(4-chloro-2,5-difluorophenyl)thieno[3,2-d]pyrimidine-4(1H)-one and phosphorus oxychloride was stirred for four hours at 90° C. to give 4-chloro-2-(4-chloro-2,5-difluorophenyl)thieno[3,2-d]pyrimidine.

The compounds shown in Tables 9 and 10 were manufactured according to a similar manner to that of Reference Example 10.

TABLE 9

| Rf | Structure | Data |
|---|---|---|
| 10 | (4-chloro-2-(4-chloro-2,5-difluorophenyl)thieno[3,2-d]pyrimidine) | MS: 317 |
| 10-1 | (4-chloro-2-(4-chloro-3,5-difluorophenyl)thieno[3,2-d]pyrimidine) | MS: 317 |
| 10-2 | (4-chloro-2-(2,4,5-trifluorophenyl)thieno[3,2-d]pyrimidine) | MS: 301 |
| 10-3 | (4-chloro-2-(4-chlorophenyl)thieno[3,2-d]pyrimidine) | MS: 281 |

TABLE 9-continued

| Rf | Structure | Data |
|---|---|---|
| 10-4 | 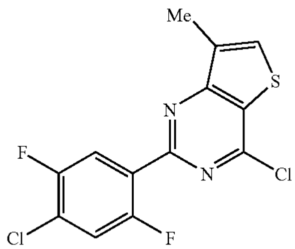 | MS: 331 |
| 10-5 | 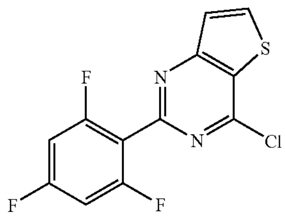 | MS: 301 |
| 10-6 | 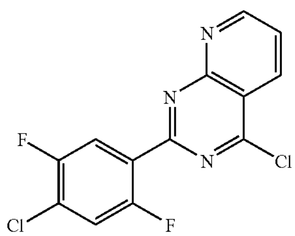 | |
| 10-7 | 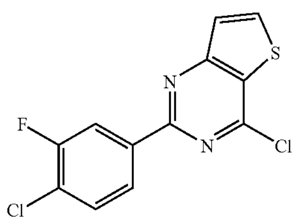 | MS: 399 |
| 10-8 | 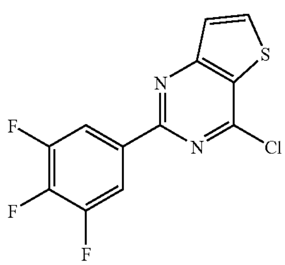 | MS: 301 |
| 10-9 | 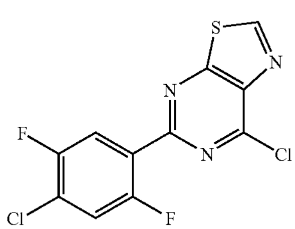 | |

TABLE 9-continued

| Rf | Structure | Data |
|---|---|---|
| 10-10 | | MS: 265 |
| 10-11 | | MS: 315 |
| 10-12 | | |
| 10-13 | | MS: 283 |

TABLE 10

| Rf | Structure | Data |
|---|---|---|
| 10-14 | 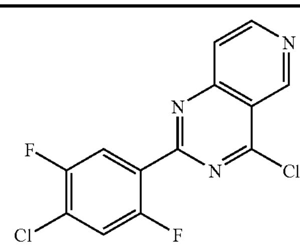 | MN: 311 |
| 10-15 | 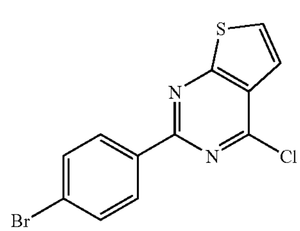 | MS: 325, 327 |

TABLE 10-continued

| Rf | Structure | Data |
|---|---|---|
| 10-16 | 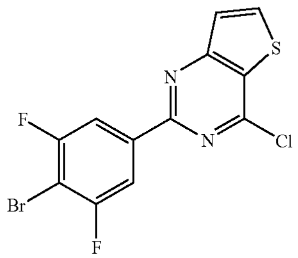 | MS: 362 |
| 10-17 | 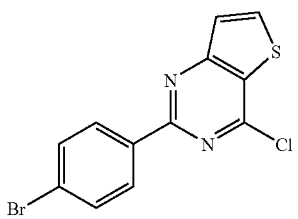 | MS: 325, 327 |
| 10-18 | 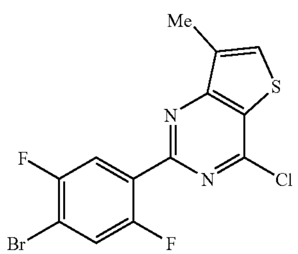 | MS: 377 |
| 10-19 | 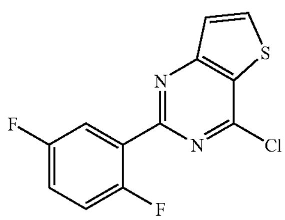 | MS: 283 |
| 10-20 | 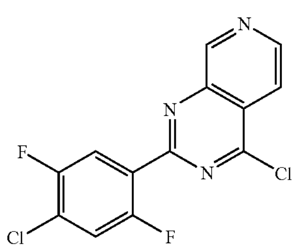 | MS: 311 |
| 10-21 | 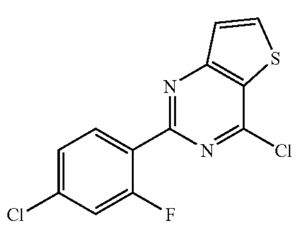 | MS: 299 |

Reference Example 11

Triethylamine and methanesulfonyl chloride were added to a chloroform solution of methyl 4,5-dichloro-2-(4-oxo-3,4-dihydrothieno[3,2-d]pyrimidine-2-yl)benzoate under ice cooling and stirred under ice cooling for 30 minutes to give methyl 4,5-dichloro-2-{4-[(methanesulfonyl)oxy]thieno[3,2-d]pyrimidine-2-yl}benzoate.

MS: 435

Reference Example 12

A solution of tert-butanol of N-methylmorpholine-N-oxide and osmium tetroxide was added to a mixture of 1-benzyl-4-methyleneazepane hydrochloride and THF-water and stirred at room temperature for 24 hours. Then the reaction solution was processed with 4M hydrochloric acid (HCl)-ethyl acetate (EtOAc) solution to give 1-benzyl-4-(hydroxymethyl)azepane-4-ol hydrochloride. 10% palladium carbon was added to a solution of EtOH of the obtained 1-benzyl-4-(hydroxymethyl)azepane-4-ol hydrochloride and stirred for six hours at room temperature under the hydrogen atmosphere to give 4-(hydroxymethyl)azepane-4-ol hydrochloride.

MS: 146

Reference Example 13

Sodium hydride and 1-benzylazepane-3-one were added to a THF solution of ethyl diethoxyphosphorylacetate under ice cooling and stirred for two hours at room temperature to give a stereoisomeric mixture of ethyl(1-benzylazepane-3-ylidene)acetate. After the obtained stereoisomeric mixture of ethyl(1-benzylazepane-3-ylidene)acetate was processed with 4M HCl-EtOAc solution, EtOH and 10% palladium carbon were added and stirred for 15 hours at room temperature under the hydrogen atmosphere to give ethyl azepane-3-ylacetate hydrochloride.

MS: 186

Reference Example 14

A mixture of 1-tert-butoxycarbonylpiperidine-4-ol, sodium hydride and DMF was stirred for 5 minutes at room temperature, then 2-chloro-N,N-dimethylethylamine was added to the resultant and further stirred for 30 minutes at room temperature to give 2-[(1-tert-butoxycarbonylpiperidine-4-yl)oxy]-N,N-dimethylethylamine. A mixture of the obtained 2-[(1-tert-butoxycarbonylpiperidine-4-yl)oxy]-N,N-dimethylethylamine and 4M HCl-dioxane solution was stirred for 7 hours at room temperature to give N,N-dimethyl-2-(piperidine-4-yloxy)ethylamine dihydrochloride.

MS: 273

Reference Example 15

A mixture of 1-tert-butoxycarbonylpiperidine-4-ol, triethylamine, benzenesulfonyl chloride and methylene chloride was stirred for two days at room temperature to give 1-tert-butoxycarbonylpiperidine-4-ylbenzenesulfonate. A mixture of the obtained 1-tert-butoxycarbonylpiperidine-4-ylbenzenesulfonate, diethyl malonate, 20% sodium ethoxide-EtOH solution and EtOH was stirred for 22 hours heated to reflux to give diethyl[1-(tert-butoxycarbonyl)piperidine-4-yl]malonate. A mixture of the obtained diethyl[1-(tert-butoxycarbonyl)piperidine-4-yl]malonate, lithium borohydride, toluene and THF was stirred for 18 hours at 60° C. to give 2-(1-tert-butoxycarbonylpiperidine-4-yl)propane-1,3-diol. A mixture of the obtained 2-(1-tert-butoxycarbonylpiperidine-4-yl)propane-1,3-diol, 4M HCl-dioxane solution and MeOH was stirred for one hour at room temperature to give 2-piperidine-4-ylpropane-1,3-diol hydrochloride.

MS: 160

Reference Example 16

A mixture of (1-tert-butoxycarbonylpiperidine-4,4-diyl) dimethanol, 4M HCl-dioxane solution and MeOH was stirred for two hours at room temperature to give piperidine-4,4-diyldimethanol hydrochloride.

MS: 146

Reference Example 17

A mixture of 1-tert-butoxycarbonyl-4-(3-hydroxypropyl) piperidine-4-ol and 4M HCl-dioxane solution was stirred for 3.5 hours at room temperature to give 4-3-hydroxypropyl) piperidine-4-ol hydrochloride.

MS: 160

Reference Example 18

A mixture of 1-tert-butoxycarbonyl piperidine-4-one and N,N-dimethylformamide dimethylacetal was stirred for 6 hours heated to reflux to give 1-tert-butoxycarbonyl-3-[(dimethylamino)methylene]piperidine-4-one. A mixture of the obtained 1-tert-butoxycarbonyl-3-[(dimethylamino)methylene]piperidine-4-one, 2-hydrazinoethanol and MeOH was stirred for two hours heated to reflux to give a mixture of 2-(5-tert-butoxycarbonyl-4,5,6,7-tetrahydro-2H-pyrazolo[4,3-c]pyridine-2-yl)ethanol and 2-(5-tert-butoxycarbonyl-4,5,6,7-tetrahydro-1H-pyrazolo[4,3-c]pyridine-1-yl)ethanol. A mixture of the obtained mixture, 4M HCl-EtOAc solution and EtOH was stirred for two hours at room temperature to give a mixture of 2-(4,5,6,7-tetrahydro-2H-pyrazolo[4,3-c]pyridine-2-yl)ethanol dihydrochloride and 2-(4,5,6,7-tetrahydro-1H-pyrazolo[4,3-c]pyridine-1-yl)ethanol dihydrochloride.

ES-MS(+): 168

Reference Example 19

A mixture of ethyl (2E)-(1-benzyl-3-methylpiperidine-4-ylidene)acetate, 1-chloroethyl chloroformate and 1,2-dicholoroethane was stirred for 30 minutes heated to reflux and concentrated under reduced pressure. The residue was dissolved in EtOH and stirred for 10 minutes heated to reflux to give ethyl (2E)-(3-methylpiperidine-4-ylidene)acetate.

MS: 184

Reference Example 20

A mixture of 1-tert-butoxycarbonylpiperazine, 3-hydroxypropionic acid, 1-hydroxybenzotriazole (HOBt), 1-ethyl-3-(3-dimethylaminopropyl)carbodiimide hydrochloride (EDCI) and DMF was stirred for 24 hours at room temperature to give 3-(4-tert-utoxycarbonylpiperazine-1-yl)-3-oxopropane-1-ol. A mixture of the obtained 3-(4-tert-butoxycarbonylpiperazine-1-yl)-3-oxopropane-1-ol, 4M HCl-dioxane solution and MeOH was stirred for 16 hours at room temperature to give 3-oxo-3-piperazine-1-ylpropane-1-ol hydrochloride.

MS: 159

Example 1

A mixture of 9.52 g of 4-chloro-2-(4-chloro-2,5-difluorophenyl)thieno[3,2-d]pyrimidine, 3.13 g of hexamethyleneimine, 10.50 ml of diisopropyl ethylamine and 190 ml of acetonitrile was stirred for 5 hours at 70° C. 600 ml of water was added to the reaction mixture and the precipitate was filtered, washed with water and dried at 50° C. under reduced pressure. The obtained solid was dissolved in 40 ml of THF. The solution was added to 15 ml of 4M HCl-EtOAc solution and concentrated under reduced pressure to give a solid. Through recrystallization of this solid from EtOH-ether, 10.97 g of 4-azepane-1-yl-2-(4-chloro-2,5-difluorophenyl) thieno[3,2-d]pyrimidine hydrochloride was obtained.

Example 2

A mixture of 160 mg of 4-chloro-2-(4-chloro-2,5-difluorophenyl)-7-methylthieno[3,2-d]pyrimidine, 2 ml of diisopropyl ethylamine and 1 ml of piperidine was stirred respectively for 17 hours at 60° C., 8 hours at room temperature and 24 hours at 95° C. 30 ml of water was added to the reaction mixture and extracted with twice of 60 ml of EtOAc. After the organic layer was dried over anhydrous magnesium sulfate, the solvent was removed under reduced pressure. The obtained residue was purified by silica gel column chromatography (hexane-EtOAc). 10 ml of THF and 1 ml of 4M HCl-EtOAc solution were added to the obtained compound. The solvent was removed under reduced pressure and the residue was recrystallized from EtOH-EtOAc to give 78 mg of 2-(4-chloro-5-fluoro-2-piperidine-1-ylphenyl)-7-methyl-4-piperidine-1-ylthieno[3,2-d]pyrimidine dihydrochloride.

Example 3

A mixture of 500 mg of 4-azepane-1-yl-2-(4-chloro-2,5-difluorophenyl)thieno[3,2-d]pyrimidine and 2M dimethylamine-THF solution was stirred for 44 hours at 80° C. 100 ml of water was added to the reaction mixture and extracted three times with 100 ml of chloroform. After the obtained organic layer washed with a saturated saline solution and dried over anhydrous magnesium sulfate, the solvent was removed under reduced pressure. The obtained residue was purified by silica gel column chromatography (hexane-EtOAc) to give a solid-15 ml of EtOAc and 5 ml of 4M HCl-EtOAc solution were added to this solid and stirred at room temperature. The precipitated white solid was filtered and recrystallized from EtOH to give 98 mg of [2-(4-azepane-1-ylthieno[3,2-d]pyrimidine-2-yl)-5-chloro-4-fluorophenyl]dimethylamine hydrochloride

Example 4

A mixture of 1.41 g of 4-chloro-2-(4-chloro-2,5-difluorophenyl)thieno[3,2-d]pyrimidine, 1.28 g of a mixture of 2-(4,5,6,7-tetrahydro-1H-pyrazolo[4,3-c]pyridine-1-yl) ethanol and 2-(4,5,6,7-tetrahydro-2H-pyrazolo[4,3-c]pyridine-2-yl)ethanol, 3.87 ml of diisopropyl ethylamine and 30 ml of acetonitrile was stirred for 12 hours at 80° C. After 100 ml of water was added to the reaction mixture and extracted with EtOAc, the organic layer was dried over anhydrous magnesium sulfate and the solvent was removed under reduced pressure. The obtained residue was purified by silica gel column chromatography (chloroform-MeOH) and 1.19 g of a foam-like substance was obtained. A mixture of the obtained foam-like substances 10 ml of pyridine and 0.62 ml of benzoyl chloride was stirred for one hour at room temperature. After 50 ml of water was added to the reaction mixture and extracted with EtOAc-THF mixed solvents the organic layer was dried over anhydrous magnesium sulfate and the solvent was removed under reduced pressure. The obtained residue was recrystallized from EtOAc and the mother liquid was repeated recrystallization from EtOAc to give 716 mg of 2-{5-[2-(4-chloro-2,5-difluorophenyl)thieno[3,2-d]pyrimidine-4-yl]-4,5,6,7-tetrahydro-2H-pyrazolo[4,3-c]pyridine- 2-yl}ethyl benzoate was obtained. Further, this recrystallized mother liquid washed with ether-hexane mixed solvent and the washed liquid was concentrated under reduced pressure to give 636 mg of 2-{5-[2-(4-chloro-2,5-difluorophenyl)thieno [3,2-d]pyrimidine-4-yl]-4,5,6,7-tetrahydro-1H-pyrazolo[4, 3-c]pyridine-1-yl}ethyl benzoate. 716 mg of the obtained 2-{5-[2-(4-chloro-2,5-difluorophenyl)thieno-[3,2-d]pyrimidine-4-yl]-4,5,6,7-tetrahydro-2H-pyrazolo[4,3-c]pyridine-2-yl}ethyl benzoate was dissolved in 10 ml of THF-EtOH (2:1) solution and was added to 2.60 ml of 1M NaOH aq. The resultant was stirred for one hour at 60° C. and was left to cool to room temperature. Then, 30 ml of 1M HCl aq was added and washed with ether, the aqueous layer was made alkaline with 100 ml of 1M NaOH aq. After this was extracted with EtOAc, the organic layer was dried over anhydrous magnesium sulfate and the solution was removed under reduced pressure. The obtained residue was dissolved in 20 ml of THF and 10 ml of MeOH, and was added to 3 ml of 4M HCl-dioxane solution, concentrated under reduced pressure and a solid was obtained. This solid was recrystallized from EtOH-EtOAc to give 687 mg of 2-{5-[2-(4-chloro-2,5-difluorophenyl)thieno[3,2-d]pyrimidine-4-yl]-4,5,6,7-tetrahydro-2H-pyrazolo[4,3-c]pyridine-2-yl}ethanol hydrochloride. Furthermore, the above-mentioned operation was carried out on the 636 mg of 2-{5-[2-(4-chloro-2,5-difluorophenyl) thieno[3,2-d]pyrimidine-4-yl]-4,5,6,7-tetrahydro-1H-pyrazolo[4,3-c]pyridine-1-yl}ethyl benzoate to give 180 mg of 2-{5-[2-(4-chloro-2,5-difluorophenyl)thieno[3,2-d]pyrimidine-4-yl]-4,5,6,7-tetrahydro-1H-pyrazolo[4,3-c]pyridine-1-yl}ethanol hydrochloride.

Example 5

A mixture of 1.88 g of ethyl {1-[2-(4-chloro-2,5-difluorophenyl)thieno-3,2-d)pyrimidine-4-yl]piperidine-3-yl}acetate, 6.20 ml of 1M NaOH aq and 20 ml of THF-EtOH (1:1) was stirred for 19 hours at room temperature. 6.20 ml of 1M HCl aq and 50 ml of water were added to the reaction mixture and further stirred for one hour at room temperature. After the precipitate was filtered and washed with water, it was dried under reduced pressure at 50° C. to give 1.77 g of {1-[2-(4-chloro-2,5-difluorophenyl)thieno[3,2-d]pyrimidine-4-yl]piperidine-3-yl}acetic acid. 650 mg of the obtained {1-[2-(4-chloro-2,5-difluorophenyl)thieno[3,2-d]pyrimidine-4-yl]piperidine-3-yl}acetic acid was dissolved in 10 ml of THF, and was added to 2 ml of 4M HCl-dioxane solution. The resultant was concentrated under reduced pressure and a solid was obtained. This solid was recrystallized from iPrOH-ether to give 672 mg of {1-[2-4-chloro-2,5-difluorophenyl)thieno[3,2-d]pyrimidine-4-yl]piperidine-3-yl}acetic acid hydrochloride.

Example 6

A mixture of 676 mg of ethyl {1-[2[(4-chloro-2,5-difluorophenyl)thieno[3,2-d]pyrimidine-4-yl]piperidine-4-ylidene]acetate, 10 ml of 6M HCl aq and 10 ml of THF was stirred all night at 90° C. After the precipitated colorless solid was filtered and washed with water and diethyl ether, it was recrystallized from acetonitrile and water to give 276 mg of {1-[2-(4-chloro-2,5-difluorophenyl)thieno[3,2-d]pyrimidine-4-yl]piperidine-4-ylidene}acetic acid hydrochloride.

Example 7

A mixture of 1.16 g of 1-tert-butoxycarbonyl-4-[2-(4-chloro-2,5-difluorophenyl)thieno[3,2-d]pyrimidine-4-yl] piperazine and 10 ml of 4M HCl-dioxane solution was stirred for two days at room temperature. 10 ml of EtOAc was added to the reaction mixture. After the precipitate was filtered and washed with EtOAc, it was dried under reduced pressure to give 1.17 g of 2-(4-chloro-2,5-difluorophenyl)-4-piperazine-1-ylthieno[3,2-d]pyrimidine dihydrochloride.

Example 9

A mixture of 451 mg of 8-[2-(4-chloro-2,5-difluorophenyl)thieno[3,2-d]pyrimidine-4-yl]-1,4-dioxa-8-azaspiro [4.5]decane, 20 mg of p-toluenesulfonic acid monohydrate and 8 ml of acetonitrile-acetone (1:1) was stirred for 5 hours heated to reflux. The reaction mixture was allowed to cool to room temperature and was added to 200 ml of water. After the precipitate was filtered and washed with water, it was dried at 50° C. under reduced pressure. The obtained solid was dissolved in 12 ml of THF and added 2 ml of 4M HCl-dioxane solution. The resultant was concentrated under reduced pressure to give a solid. This solid washed with acetonitrile-ether to give 310 mg of 1-[2-(4-chloro-2,5-difluorophenyl)thieno [3,2-d]pyrimidine-4-yl]piperidine-4-one hydrochloride.

Example 10

A mixture of 500 mg of 2-(4-chloro-2,5-difluorophenyl)-4-piperazine-1-ylthieno[3,2-d]pyrimidine dihydrochloride, 104 mg of hydroxyacetic acid, 0.32 ml of triethylamine, 184 mg of HOBt, 261 mg of EDCI and 10 ml of DMF was stirred for two days at room temperature. 70 ml of water was added to the reaction mixture. After the precipitate was filtered and washed with water, it was dried at 50° C. under reduced pressure. The obtained solid was dissolved in 10 ml of THF and was added to 2 ml of 4M HCl-dioxane aq. The resultant was concentrated under reduced pressure to give a solid. This solid was recrystallized from EtOH-EtOAc to give 487 mg of 2-{4-[2-(4-chloro-2,5-difluorophenyl)thieno[3,2-d]pyrimidine-4-yl]piperazine-1-yl}-2-oxoethanol hydrochloride.

Example 11

0.14 ml of ethyl 2-chloro-2-oxoacetate was added to a mixture of 500 mg of 2-(4-chloro-2,5-difluorophenyl)-4-piperazine-1-ylthieno[3,2-d]pyrimidine dihydrochloride, 0.99 ml of diisopropylethylamine and 10 ml of DMF and stirred for one hour at room temperature. 50 ml of water was added to the reaction mixture and extracted with EtOAc. After the organic layer was washed with a saturated saline solution, the solvent was removed under reduced pressure to give 619 ma of residue. 219 mg of this residue was dissolved in 10 ml of THF and added to 2 ml of 4M HCl-EtOAc. The solvent was removed under reduced pressure and the obtained residue washed with EtOH and EtOAc to give 185 mg of ethyl {4-[2-(4-chloro-2,5-difluorophenyl)thieno[3,2-d]pyrimidine-4-yl]piperazine-1-yl}(oxo)acetate hydrochloride.

Example 12

A mixture of 50 mg of 2-(4-chloro-2,5-difluorophenyl)-4-(3-methylpiperazine-1-yl)thieno[3,2-d]pyrimidine dihydrochloride and 1 ml of pyridine was cooled with ice, and added to 0.05 ml of acetic anhydro-de. The resultant was stirred for 1.5 hours at room temperature. After the solvent was removed under reduced pressure, the obtained residue washed with water to give 43 mg of 4-(4-acetyl-3-methylpiperazine-1-yl)-2-(4-chloro-2,5-difluorophenyl)thieno[3,2-d]pyrimidine.

Example 13

A mixture of 500 mg of {1-[2-(4-chloro-2,5-difluorophenyl)thieno[3,2-d]pyrimidine-4-yl]piperidine-4-yl}acetic acid hydrochloride, 316 mg of ammonium chloride, 0.82 ml of triethylamine, 319 mg of HOBt, 452 mg of EDCI and 10 ml of DMF was stirred for 5 days at room temperature. 60 ml of water was added to the reaction mixture and after the precipitate was filtered and washed with water, it was dried at 50° C. under reduced pressure. The obtained solid was dissolved in 10 ml of THF and was added to 2 ml of 4M HCl-dioxane solution. The resultant was concentrated under reduced pressure to give a solid. This solid washed with ether to give 573 mg of 2-{1-[2-(4-chloro-2,5-difluorophenyl)thieno[3,2-d]pyrimidine-4-yl]piperidine-4-yl}acetamido hydrochloride.

Example 14

A mixture of 530 mg of 1-[2-(4-chloro-2,5-difluorophenyl)thieno[3,2-d]pyrimidine-4-yl]azepane-4-one, 60 mg of sodium borohydride, 20 ml of THF and 20 ml of EtOH was stirred for 45 minutes at room temperature. After the reaction mixture was concentrated under reduced pressure, 50 ml of water was added to the residue and extracted twice with 100 ml of EtOAc. After the organic layer washed with a saturated saline solution, the solvent was removed under reduced pressure and 20 ml of THF, 20 ml of EtOH and 0.5 ml of 4M HCl-EtOAc solution were added to the obtained residue. The solvent was removed under reduced pressure, the obtained residue washed with EtOH and EtOAc to give 433 mg of 1-[2-(4-chloro-2,5-d-fluorophenyl)thieno[3,2-d]pyrimidine-4-yl]azepane-4-ol hydrochloride.

Example 15

440 mg of potassium tert-butoxide was added to a mixture of 650 mg of 1-[2-(4-chloro-2,5-difluorophenyl)thieno[3,2-d]pyrimidine-4-yl]azepane-4-one, 380 mg of p-toluensulfonylmethyl isocyanide, 20 ml of 1,2-dimethoxyethane and 10 ml of THF and the resultant was stirred for one hour under ice cooling. After the reaction mixture was concentrated under reduced pressure, 50 ml of water was added to the obtained residue and extracted twice with 100 ml of EtOAc. After the organic layer washed with a saturated saline solution and dried over anhydrous magnesium sulfate, the solvent was removed under reduced pressure. The obtained residue was purified by silica gel column chromatography chloroform-MeOH) and a foam-like substance was obtained. 50 ml of EtOAc and 0.5 ml of 4M HCl-EtOAc solution were added to the foam-like substance and the solvent was removed under reduced pressure to give a solid. The obtained solid was washed with ethyl acetate to give 150 mg of 1-[2-(4-chloro-2,5-difluorophenyl)thieno[3,2-d]pyrimidine-4-yl]azepane-4-carbonitrile hydrochloride.

Example 16

A mixture of 870 mg of 2-(4-chloro-2,5-difluorophenyl)-4-piperazine-1-ylthieno[3,2-d]pyrimidine, 1.08 ml of (R)-glycidol and 15 ml of THF was stirred for 21 hours heated to reflux. The reaction mixture was concentrated under reduced pressure and the obtained residue was purified by silica gel column chromatography (chloroform-MeOH) to give a foam-like substance. After the obtained foam-like substance was dissolved in 10 ml of EtOH and was added to 2 ml of 4M HCl-dioxane solution, it was concentrated under reduced pressure to give a solid. This solid was recrystallized from ethanol to give 898 mg of (S)-3-{4-[2-(4-chloro-2,5-difluorophenyl)thieno[3,2-d]pyrimidine-4-yl]piperazine-1-yl}propane-1,2-diol dihydrochloride.

Example 17

A mixture of 1.06 g of 1-[2-(4-chloro-2,5-difluorophenyl)thien[3,2-d]pyrimidine-4-yl]azepane-4-one, 220 mg of hydroxylamine hydrochloride, 260 mg of sodium acetate, 3 ml of waters 30 ml of iPrOH and 30 ml of DMF was stirred for one hour at 100° C. After the reaction mixture was concentrated under reduced pressures 100 ml of water was added to the residue and extracted twice with 200 ml of EtOAc. After the organic layer washed with a saturated saline solution and dried over anhydrous magnesium sulfates the solvent was removed under reduced pressure to give 542 mg of a solid. 10 ml of THF 10 ml of EtOH and 0.5 ml of 4M HCl-EtOAc solution were added to the obtained solid. After the solvent was removed under reduced pressure, the obtained residue washed with ether to give 162 mg of 1-[2-(4-chloro-2,5-difluorophenyl)thieno[3,2-d]pyrimidine-4-yl]azepane-4-oneoxime hydrochloride.

Example 18

A mixture of 260 mg of 1-[2-(4-chloro-2,5-difluorophenyl)thieno[3,2-d]pyrimidine-4-yl]azepane-4-carbonitrile and 35% HCl aq was stirred for 3 hours at 80° C. After the reaction mixture was concentrated and dried under reduced pressure, the obtained residue was purified by silica gel column chromatography (chloroform-MeOH) to give a solid. THF and 0.2 ml of 4M HCl-EtOAc solution were added to the obtained solid. After the solvent was removed under reduced pressure, the residue washed with EtOAc to give 250 mg of 1-[2-(4-chloro-2,5-difluorophenyl)thieno[3,2-d]pyrimidine-4-yl]azepane-4-carboxylic acid hydrochloride.

Example 19

A mixture of 1.07 g of tert-butyl ({1-[2-(4-chloro-2,5-difluorophenyl)thieno[3,2-d]pyrimidine-4-yl}oxy)acetate, 20 ml of 4M HCl-EtOAc solution and 20 ml of EtOH was stirred for 18 hours at room temperature. The reaction mixture was concentrated under reduced pressure and the obtained residue was recrystallized from EtOH-ether to give 855 mg of ethyl ({1-[2-(4-chloro-2,5-difluorophenyl)thieno[3,2-d]pyrimidine-4-yl]piperidine-4-yl}oxy)acetate hydrochloride.

Example 20

A mixture of 582 mg of 2-(4-chloro-2,5-difluorophenyl)-4-(2,3,6,7-tetrahydro-1H-azepine-1-yl)thieno[3,2-d]pyrimidine, 235 mg of N-methylmorpholine-N-oxide, 1.30 ml of 2.5 w % osmium tetroxide-tert-butanol solution and 10 ml of THF-water (4:1) was stirred for 20 hours at room temperature. After 50 ml of water was added to the reaction mixture and extracted with EtOAc, the resultant washed with a saturated saline solution. After the organic layer was dried over anhydrous magnesium sulfate, the solvent was removed under reduced pressure. the obtained residue was purified by silica gel column chromatography (chloroform-MeOH) to give a foam-like substance. After the obtained foam-like substance was dissolved in 20 ml of THF and 2 ml of 4M HCl-EtOAc solution was added, it was concentrated under reduced pressure to give a solid. This solid was recrystallized from EtOH-ether to give 618 mg of (4RS,5SR)-1-[2-(4-chloro-2, 5-difluorophenyl)thieno[3,2-d]pyrimidine-4-yl]azepane-4, 5-diol hydrochloride.

Example 21

3.65 ml of THF solution with 1.0M diisobutylaluminum hydride was added dropwise under ice cooling into a mixture of 400 mg of ethyl 4-[2-(4-chloro-2,5-difluorophenyl)thieno [3,2-d]pyrimidine-4-yl]piperazine-2-carboxylate and 10 ml of THF and the resultant was stirred for 3 hours at room temperature. After 10 ml of 1M HCl aq was added to the reaction mixture and stirred for 10 minutes at room temperature, 20 ml of 1M NaOH aq was added and extracted with chloroform. After the organic layer was dried over anhydrous magnesium sulfate, the solvent was removed under reduced pressure. The obtained residue was purified by silica gel column chromatography (chloroform-MeOH) to give an oily substance. After the obtained oily substance was dissolved in 10 ml of THF and 1 ml of 4M HCl-dioxane solution was added, the resultant was concentrated under reduced pressure to give a solid. This solid washed with EtOH-ether to give 60 mg of {4-[2-(4-chloro-2,5-difluorophenyl)thieno[3,2-d]pyrimidine-4-yl]piperazine-2-yl}methanol dihydrochloride.

Example 22

805 mg of carbonyldiimidazole was added to a suspension of 10 ml of DMF with 496 mg of 4-[2-(4-chloro-2,5-difluorophenyl)thieno[3,2-d]pyrimidine-4-yl]piperazine-2-carboxamide and the resultant was stirred for 7 hours at room temperature. 50 ml of water was added to the reaction mixture and the precipitate was filtered, washed with water and dried at 50° C. under reduced pressure. After the obtained solid was dissolved in 8 ml of DMF, 150 mg of potassium tert-butoxide was added and the resultant was stirred for 30 minutes at room temperature. 15 ml of 10% citric acid solution and 50 ml of water were added to the reaction mixture and the precipitate was filtered, washed with water and was dried at 50° C. under reduced pressure. After the obtained solid was dissolved in 20 ml of THF, 2 ml of 4M HCl-dioxane solution was added and the resultant was concentrated under reduced pressure to give a solid. This solid washed with EtOH-ether to give 573 mg of 7-[2-(4-chloro-2,5-difluorophenyl)thieno[3,2-d]pyrimidine-4-yl]-tetrahydroimidazo[1,5-a]piperazine-1,3(2H, 5H)-dione hydrochloride.

Example 23

48 mg of sodium hydroxide (60% suspended oil matter) was added to a mixture of 290 mg of ethyl 1-acetyl-4-[2-(4-chloro-2,5-difluorophenyl)thieno[3,2-d]pyrimidine-4-yl] piperazine-2-carboxylate and 6 ml of THF and the resultant was stirred for one hour at room temperature and further stirred for one hour at 70° C. After the reaction mixture was allowed to cool to room temperature, 20 ml of water and 20 ml of a 10% citric acid solution were added and the resultant was extracted with chloroform. After the organic layer was dried over anhydrous magnesium sulfate, the solvent was removed under reduced pressure and the obtained residue washed with ether-chloroform. After the obtained solid was dissolved in 10 ml of THF and 2 ml of 4M HCl-dioxane solution was added, the resultant was concentrated under reduced pressure to give a solid. This solid was recrystallized from EtOH-ether to give 82 mg of 2-[2-(4-chloro-2,5-difluorophenyl)thieno[3, 2-d]pyrimidine-4-yl]tetrahydropyrrolo[1,2-a]piperazine-6,8 (2H, 7H)-dione hydrochloride.

Example 24

3.32 ml of 1.59M n-butyllithium-hexane solution was added dropwise for 5 minutes at −78° C. into a mixture of 1.82 g of 4-azepane-1-yl-2-(4-chloro-2,5-difluorophenyl)thieno [3,2-d]pyrimidine and 40 ml of THF and stirred for 15 minutes. Approximately 50 g of crushed dry ice was added to the reaction mixture and the temperature subsequently raised to room temperature. 50 ml of 10% citric acid solution was added to the reaction mixture and extracted with EtOAc. After the organic layer washed with a saturated saline solution and dried over anhydrous magnesium sulfate, the solvent was removed under reduced pressure. The obtained residue was purified by silica gel column chromatography (chloroform-MeOH) to give a foam-like substance. The foam-like substance was recrystallized from THF-acetonitrile to give 288 g of 4-azepane-1-yl-2-(4-chloro-2,5-difluorophenyl)thieno[3, 2-d]pyrimidine-6-carboxylic acid.

Example 25

0.69 ml of trifluoroacetic anhydride was added to 20 ml of THF suspension with 1.02 g of 2-{1-[2-(4-chloro-2,5-difluorophenyl)thieno[3,2-d]pyrimidine-4-yl]piperidine-4-yl}acetoamide and the resultant was stirred for 10 minutes at room temperature. 50 ml of saturated sodium hydrogen carbonate aqueous solution was added to the reaction mixture and the resultant was extracted with EtOAc. After the organic layer was washed with a saturated saline solution and dried over anhydrous magnesium sulfate, the solvent was removed under reduced pressure to give 975 mg of a pale yellow solid. After 150 mg of this solid was dissolved in 5 ml of THF and 1 ml of 4M HCl-dioxane solution was added, the resultant was concentrated under reduced pressure to give a solid. This solid washed with acetonitrile-ether to give 156 mg of {1-[2-(4-chloro-2,5-difluorophenyl)thieno[3,2-d]pyrimidine-4-yl] piperidine-4-yl}acetonitrile hydrochloride.

Example 26

A mixture of 825 mg of {1-[2-(4-chloro-2,5-difluorophenyl)thieno[3,2-d]pyrimidine-4-yl]piperidine-4-yl}acetonitrile, 15 ml of N-methylpyrrolidinone, 1.32 g of sodium azide and 2.81 g of triethylamide hydrochloride was stirred for 8 hours at 150° C. After the reaction mixture was allowed to cool to room temperature, 50 ml of water was added and the resultant was extracted with EtOAc. After the organic layer washed with a saturated saline solution and dried over anhydrous magnesium sulfate, the solvent was removed under reduced pressure. The obtained residue was purified by silica gel column chromatography (chloroform-MeOH) to give an oily substance. After the obtained oily substance was dissolved in 10 ml of THF and 4 ml of 4M HCl-dioxane solution was added, the resultant was concentrated under reduced pressure to give a solid. The obtained solid was recrystallized from iPrOH-EtOAc-ether to give 868 mg of 2-(4-chloro-2,5-difluorophenyl)-4-[4-(1H-tetrazole-5-ylmethyl)piperidine-1-yl]thieno[3,2-d]pyrimidine hydrochloride.

Example 27

A mixture of 514 mg of 4-azepane-1-yl-2-(4-chloro-2,5-difluorophenyl)thieno[3,2-d]pyrimidine, 300 mg of sodium methoxide and 10 ml of MeOH was stirred in a sealed tube for 5 days at 120° C. After the reaction mixture was concentrated under reduced pressure, 40 ml of water was added to the obtained residue and extracted twice with 40 ml of chloroform. After the organic layer washed with a saturated saline solution and dried over anhydrous magnesium sulfate, the solvent was removed under reduced pressure. The obtained residue was purified by silica gel column chromatography (chloroform-MeOH) to give a solid. After 0.6 ml of 4M HCl-dioxane solution was added to 10 ml of chloroform-MeOH with this solid, the resultant was concentrated under reduced pressure to give a solid. After the obtained solid was recrystallized three times from EtOAc and EtOH, the crystal generated was filtered and washed with EtOAc to give 223 mg of 4-azepane-1-yl-2-(4-chloro-5-fluoro-2-methoxyphenyl)thieno[3,2-d]pyrimidine hydrochloride.

The compounds given in Tables 11 to 30 below were prepared using the above methods, methods obvious to those skilled in the art, or modified methods thereof. Chemical structures and spectral data of these compounds in Examples are shown in Tables. Symbols in Tables have the following meanings (ditto hereinafter).

Ex: Example number (a line wherein only a numeral is given in the column of Ex means that the compound in said Example number is hydrochloride, whereas a line wherein a numeral is followed by slash (/) and "f" means that the compound in said Example number is a free form.)

TABLE 11

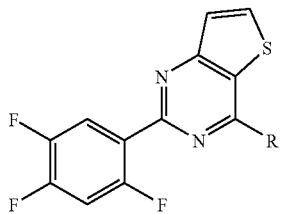

| Ex | R | Data |
|---|---|---|
| 29 | pipe | MS: 350 |
| 30 | mor | MS: 352 |
| 31 | tmor | MS: 368 |
| 32 | 4-(HO$_2$CCH$_2$)-pipe | MS: 408 |
| 33/f | 4-(EtO$_2$CCH$_2$)-pipe | |
| 34 | (S)-3-(HO$_2$CCH$_2$)-pipe | MS: 408 |
| 35/f | (S)-3-(EtO$_2$CCH$_2$)-pipe | |
| 36 | 4-(HO$_2$C(CH$_2$)$_2$)-pipe | MS: 422 |
| 37/f | 4-(EtO$_2$C(CH$_2$)$_2$)-pipe | MS: 450 |
| 38 | (S)-3-(HO$_2$C(CH$_2$)$_2$)-pipe | MS: 422 |
| 39/f | (S)-3-(EtO$_2$C(CH$_2$)$_2$)-pipe | MS: 450 |
| 40 | 4-(HO$_2$C(CH$_2$)$_3$)-pipe | MS: 436 |
| 41/f | 4-(EtO$_2$C(CH$_2$)$_3$)-pipe | MS: 464 |
| 42 | 3-(HO$_2$C(CH$_2$)$_2$)-pyrr | MS: 408 |
| 43/f | 3-(EtO$_2$C(CH$_2$)$_2$)-pyrr | MS: 436 |
| 44 | 4-(HO$_2$CCH$_2$)-hPy | MS: 406 |
| 45/f | 4-(EtO$_2$CCH$_2$)-hPy | MS: 434 |

TABLE 12

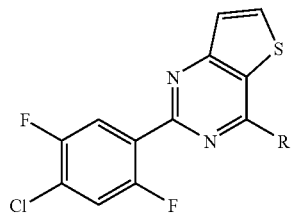

| Ex | R | Data |
|---|---|---|
| 1 | azep | MS: 380 |
| 4 | 2-(HO(CH$_2$)$_2$)-2,4,6,7-tetrahydro-5H-pyrazolo[4,3-c]pyridin-5-yl | MS: 448 |
| 4 | 1-(HO(CH$_2$)$_2$)-1,4,6,7-tetrahydro-5H-pyrazolo[4,3-c]pyridin-5-yl | MS: 448 |
| 5 | 3-(HO$_2$CCH$_2$)-pipe | MS: 424 |
| 6 | 4-(carboxymethylene)-pipe | MS: 422 |
| 7 | pipa | MS: 367 |
| 9 | 4-oxo-pipe | MS: 380 |
| 10 | 4-(HOCH$_2$CO)-pipa | MS: 425 |
| 11 | 4-(EtO$_2$CCO)-pipa | MS: 467 |
| 12/f | 4-Ac-3-Me-pipa | MS: 423 |
| 13 | 4-(H$_2$NOCCH$_2$)-pipe | MS: 423 |
| 14 | 4-HO-azep | MS: 396 |
| 15 | 4-cyano-azep | MS: 405 |
| 16 | (S)-4-(HOCH$_2$CH(OH)CH$_2$)-pipa | MS: 441 |
| 17 | 4-hydroxyimino-azep | MS: 409 |
| 18 | 4-(HO$_2$C)-azep | MS: 424 |
| 19 | 4-(EtO$_2$CCH$_2$O)-pipe | MS: 468 |
| 20 | cis-4,5-diOH-azep | MS: 412 |
| 21 | 3-(HOCH$_2$)-pipa | MS: 397 |
| 22 | 1,3-dioxohexahydroimidazo[1,5-a]pyrazin-7(1H)-yl | MS: 436 |
| 23 | 6,8-dioxohexahydropyrrolo[1,2-a]pyrazin-2(1H)-yl | MS: 435 |
| 25 | 4-(cyano-CH$_2$)-pipe | MS: 405 |
| 26 | 4-(tet-CH$_2$)-pipe | MS: 448 |
| 46 | 3-(AcHN)-pyrr | MS: 409 |
| 47 | 4-pipe-pipe | MS: 449 |
| 48 | 4-Me-pipa | MS: 381 |
| 49 | 4-(EtO$_2$C)-pipa | MS: 439 |
| 50 | 4-Me-hpipa | MS: 395 |
| 51 | 3-Ph-pipa | MS: 443 |
| 52 | 3-Bn-pipa | MS: 457 |
| 53 | (S)-3-Me-pipe | MS: 380 |

TABLE 13

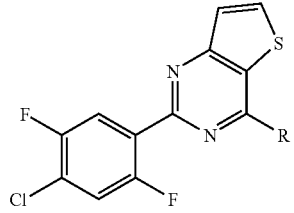

| Ex | R | Data |
|---|---|---|
| 54 | (R)-3-Me-pipe | MS: 380 |
| 55 | (R)-3-Bn-pipa | MS: 457 |
| 56 | (R)-3-iPr-pipa | MS: 409 |
| 57 | (S)-3-iPr-pipa | MS: 409 |
| 58 | 3-(3-Py)-pipa | MS: 444 |
| 59 | (R)-3-(HO$_2$CCH$_2$)-pipe | MS: 424 (ES+) |
| 60/f | (R)-3-(EtO$_2$CCH$_2$)-pipe | MS: 452 |
| 61 | (S)-3-(HO$_2$CCH$_2$)-pipe | ES-MS: 424 |
| 62/f | (S)-3-(EtO$_2$CCH$_2$)-pipe | MS: 452 |
| 63/f | 4-HO$_3$S-pipe | MS: 446 |
| 64 | 4-(HO$_2$C(CH$_2$)$_2$)-pipa | MS: 439 |
| 65/f | 4-(MeO$_2$C(CH$_2$)$_2$)-pipa | MS: 453 |

TABLE 13-continued

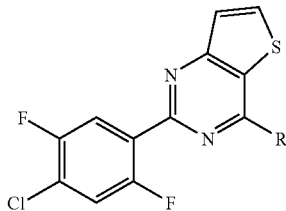

| Ex | R | Data |
|---|---|---|
| 66 | cis-2,6-diMe-mor | MS: 396 |
| 67 | (4aR,8aS)-decahydroisoquinolin-2-yl | MS: 420 |
| 68 | indolin-1-yl | MS: 400 |
| 69 | 2,5-dihydropyrrol-1-yl | MS: 350 |
| 70 | (cis-3,4-diOH)-pyrr | MS: 384 |
| 71 | 5-Boc-2,5-diazabicyclo[2.2.1]heptan-2-yl | MS: 479 |
| 72 | 2,5-diazabicyclo[2.2.1]heptan-2-yl | MS: 379 |
| 73 | 4-(HOCH$_2$)-hPy | MS: 394 |
| 74 | 4-(PhOCOCH$_2$)-hPy | MS: 498 |
| 75 | 4-oxo-azep | MS: 394 |
| 76 | 2,3,4,9-tetrahydro-1H-b-carbolin-2-yl | MS: 453 |
| 77 | 3-F$_3$C-pipa | MS: 435 |
| 78 | 4-HO-4-Me-azep | MS: 410 |
| 79 | 4-Me-azep | MS: 394 |
| 80 | 4-(EtO$_2$C)-azep | MS: 452 |
| 81 | 4-HO-4-(HOCH$_2$)-azep | MS: 426 |
| 82 | (R)-3-HO$_2$C-1,2,3,4-tetra-hydroisoquinolin-2-yl | MS: 458 |
| 83/f | (R)-3-EtO$_2$C-1,2,3,4-tetra-hydroisoquinolin-2-yl | MS: 486 |
| 84 | (S)-3-HO$_2$C-1,2,3,4-tetra-hydroisoquinolin-2-yl | MS: 458 |
| 85/f | (S)-3-EtO$_2$C-1,2,3,4-tetra-hydroisoquinolin-2-yl | MS: 486 |

TABLE 14

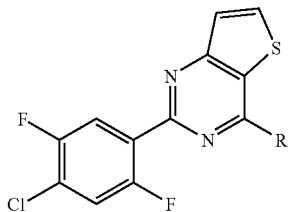

| Ex | R | Data |
|---|---|---|
| 86 | 4-((HO$_2$CCH$_2$)N(Me))-pipe | MS: 453 |
| 87/f | 4-((EtO$_2$CCH$_2$)N(Me))-pipe | MS: 481 |
| 88 | (S)-3-(HO$_2$C(CH$_2$)$_2$)-pipe | MS: 438 |
| 89/f | (S)-3-(EtO$_2$C(CH$_2$)$_2$)-pipe | MS: 466 |
| 90 | (R)-3-(HO$_2$C(CH$_2$)$_2$)-pipe | MS: 438 |
| 91/f | (R)-3-(EtO$_2$C(CH$_2$)$_2$)-pipe | MS: 466 |
| 92 | 3-(HO$_2$CCH$_2$)-azep | MS: 438 |
| 93/f | 3-(EtO$_2$CCH$_2$)-azep | MS: 466 |
| 94 | pipe | MS: 366 |
| 95 | mor | MS: 368 |
| 96 | tmor | MS: 384 |
| 97 | 1,4-oxazepan-4-yl | MS: 382 |
| 98 | pyrr | MS: 352 |
| 99 | 1,3-thiazolidin-3-yl | MS: 370 |
| 100 | hPy | MS: 364 |
| 101 | 4-Me-pipe | MS: 380 |
| 102 | 4-HO-pipe | MS: 382 |
| 103 | 3-HO-pipe | MS: 382 |
| 104 | 3-(HOCH$_2$)-pipe | MS: 396 |
| 105 | 3-(MeOCH$_2$)-pipe | MS: 410 |
| 106 | 4-(EtO$_2$C)-pipe | MS: 438 |
| 107 | 4-(HO$_2$C)-pipe | MS: 410 |
| 108 | 5-oxo-hpipa | MS: 395 |

TABLE 14-continued

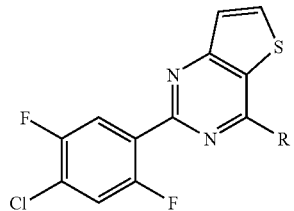

| Ex | R | Data |
|---|---|---|
| 109 | 3-(EtO$_2$C)-pipe | MS: 438 |
| 110 | 4,4-diF-pipe | MS: 402 |
| 111 | 3-Me-pipe | MS: 380 |
| 112 | 4-(HOCH$_2$)-pipe | MS: 396 |
| 113 | 4-(HO(CH$_2$)$_2$)-pipe | MS: 410 |
| 114 | 4-(HOCH$_2$CH(OH))-pipe | ES-MS: 426 |
| 115 | 4-(HO(CH$_2$)$_2$)-pipa | MS: 411 |
| 116 | 4-(HOC)-pipa | MS: 395 |
| 117 | 4-Ac-pipa | MS: 409 |
| 118 | 4-(H$_2$NOC)-pipe | MS: 409 |
| 119 | 3-(H$_2$NOC)-pipe | MS: 409 |
| 120 | 1-oxo-tmor | MS: 400 |

TABLE 15

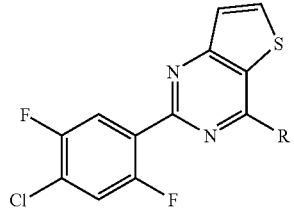

| Ex | R | Data |
|---|---|---|
| 121 | 1,1-dioxo-tmor | MS: 415 |
| 122 | (R)-3-HO-pyrr | MS: 368 |
| 123 | (S)-3-HO-pyrr | MS: 368 |
| 124 | 4-Boc-pipa | MS: 467 |
| 125 | 2-Me-pipe | MS: 380 |
| 126 | 3-HO$_2$C-pipe | MS: 410 |
| 127 | 1,4-dioxa-8-azaspiro[4.5]decan-8-yl | MS: 424 |
| 128 | 2-(HOCH$_2$)-pipe | ES-MS: 396 |
| 129 | 4-Ms-pipa | MS: 445 |
| 130 | 4-F$_3$C-pipe | MS: 434 |
| 131 | 2-(HOCH$_2$)-mor | MS: 398 |
| 132 | 3-(EtO$_2$CCH$_2$)-pipe | MS: 452 |
| 133 | 4-H$_2$N-pipe | MS: 381 |
| 134 | 4-(EtO$_2$CCH$_2$)-pipe | MS: 452 |
| 135 | 4-(HO$_2$CCH$_2$)-pipe | MS: 424 |
| 136 | 4-(EtO$_2$CCH$_2$CO)-pipa | MS: 481 |
| 137 | 4-(HO$_2$CCH$_2$CO)-pipa | MS: 453 |
| 138 | 4-(HO$_2$CCO)-pipa | MS: 439 |
| 139 | 4-(MsNH)-pipe | MS: 459 |
| 140 | 4-(AcNH)-pipe | MS: 423 |
| 141 | 4-(HOCH$_2$CONH)-pipe | MS: 439 |
| 142 | 4-(HO$_2$CCH$_2$NH)-pipe | MS: 439 |
| 143/f | 4-(EtO$_2$CCH$_2$NH)-pipe | ES-MS: 467 |
| 144 | hpipa | MS: 381 |
| 145/f | 4-Boc-hpipa | |
| 146 | (R)-4-(HOCH$_2$CH(OH)CH$_2$)-pipa | MS: 441 |
| 147 | (R)-4-(HOCH$_2$CH(OH)CH$_2$)-hpipa | MS: 455 |
| 148 | (S)-4-(HOCH$_2$CH(OH)CH$_2$)-hpipa | MS: 455 |
| 149 | 4-(Me$_2$N(CH$_2$)$_2$O)-pipe | MS: 453 |
| 150 | 4-(HO(CH$_2$)$_2$O)-pipe | MS: 426 |
| 151 | 4,4-di(HOCH$_2$)-pipe | MS: 426 |
| 152 | 4-((HOCH$_2$)$_2$CH)-pipe | MS: 440 |
| 153 | 4-(EtO$_2$CCH$_2$)-pipa | MS: 453 |
| 154 | 4-(EtO$_2$CCH(Me))-pipa | MS: 467 |
| 155 | 4-(HO(CH$_2$)$_2$)-hpipa | MS: 425 |

TABLE 16

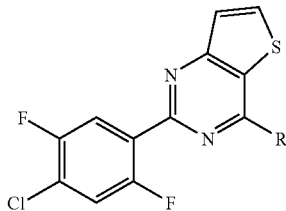

| Ex | R | Data |
|---|---|---|
| 156 | 4-(HO$_2$CCH$_2$)-3-oxo-pipa | MS: 439 |
| 157/f | 4-(tBuO$_2$CCH$_2$)-3-oxo-pipa | MS: 495 |
| 158 | 4-(HOCH$_2$CH$_2$)-pipa | MS: 425 |
| 159 | 4-(HO$_2$CCH(Me))-pipa | MS: 439 |
| 160 | 4-(HO$_2$CCH$_2$O)-pipe | MS: 440 |
| 161 | 2,3,6,7-tetrahydro-1H-azepin-1-yl | MS: 378 |
| 162 | 3-(EtO$_2$C)-pipa | MS: 439 |
| 163 | 3-(H$_2$NOC)-pipa | MS: 410 |
| 164 | 3-(Me$_2$NOC)-pipa | MS: 438 |
| 165 | 4-OH-4-(HO(CH$_2$)$_3$)-pipe | MS: 440 |
| 166 | 1-oxa-8-azaspiro[4.5]decan-8-yl | MS: 422 |
| 167 | 3-HO$_2$C-pipa | MS: 411 |
| 168 | 4-(HO(CH$_2$)$_2$N(Me))-pipe | MS: 439 |
| 169 | 4-(HO(CH$_2$)$_3$N(Me))-pipe | MS: 453 |
| 170 | 2,4,6,7-tetrahydro-5H-pyrazolo[4,3-c]pyridin-5-yl | MS: 404 |
| 171 | 7,8-dihydropyrido[4,3-d]pyrimidin-6(5H)-yl | ES-MS: 416 |
| 172 | 4-((R)-HOCH$_2$C(OH)CH$_2$)-3-((S)-Me)-pipa | ES-MS: 455 |
| 173 | 4-((S)-HOCH$_2$C(OH)CH$_2$)-3-((S)-Me)-pipa | ES-MS: 455 |
| 174 | 4-((R)-HOCH$_2$C(OH)CH$_2$)-3-((R)-Me)-pipa | ES-MS: 439 |
| 175 | 4-((S)-HOCH$_2$C(OH)CH$_2$)-3-((R)-Me)-pipa | ES-MS: 455 |
| 176 | (S)-3-(HO(CH$_2$)$_2$)-pipa | MS: 411 |
| 177 | (R)-3-(HO(CH$_2$)$_2$)-pipa | MS: 411 |
| 178 | 2,4-dioxo-1,3,8-triazaspiro[4.5]decan-8-yl | MS: 450 |
| 179 | 3-HO$_2$C-3-Me-2,4-dioxa-9-azaspiro[5.5]undecan-9-yl | MS: 496 |
| 180/f | 3-EtO$_2$C-3-Me-2,4-dioxa-9-azaspiro[5.5]undecan-9-yl | MS: 524 |
| 181 | 4-(HO$_2$C(CH$_2$)$_3$)-pipe | MS: 452 |
| 182/f | 4-(EtO$_2$C(CH$_2$)$_3$)-pipe | |
| 183 | 4-(HO(CH$_2$)$_2$NHCO)-pipe | MS: 453 |
| 184 | 4-(HO(CH$_2$)$_2$N(Me)CO)-pipe | MS: 467 |
| 185 | 4-(di(HO(CH$_2$)$_2$)NCO)-pipe | MS: 497 |
| 186 | 4-(mor-CO)-pipe | MS: 479 |
| 187 | 4-(HO(CH$_2$)$_2$CO)-pipa | ES-MS: 439 |

TABLE 17

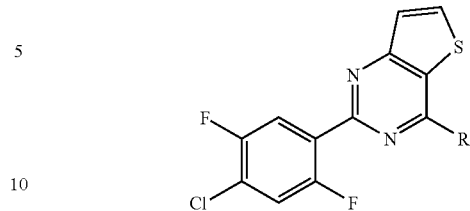

| Ex | R | Data |
|---|---|---|
| 188 | 4-(HOCH$_2$CH(OH)CO)-pipa | MS: 455 |
| 189 | 4-((HOCH$_2$)$_2$C(Me)CO)-pipa | MS: 483 |
| 190 | 3-(HO(CH$_2$)$_2$NHCO)-pipa | MS: 454 |
| 191 | 4-cyano-pipe | MS: 391 |
| 192 | 4-(HO$_2$CCH$_2$NHCO)-pipe | MS: 467 |
| 193/f | 4-(MeO$_2$CCH$_2$NHCO)-pipe | MS: 481 |
| 194 | 4-tet-pipe | MS: 434 |
| 195 | 2-(HO$_2$CCH$_2$)-tmor | MS: 442 |
| 196/f | 2-(EtO$_2$CCH$_2$)-tmor | MS: 470 |
| 197 | 1,3-dioxo-2-(HO$_2$CCH$_2$)-hexahydroimidazo[1,5-a]pyrazin-7(1H)-yl | MS: 494 |
| 198 | 1,3-dioxo-2-(tBuO$_2$CCH$_2$)-hexahydroimidazo[1,5-a]pyrazin-7(1H)-yl | MS: 550 |

TABLE 17-continued

| Ex | R | Data |
|---|---|---|
| 199 | 2-(HO$_2$CCH$_2$)-mor | MS: 426 |
| 200/f | 2-(EtO$_2$CCH$_2$)-mor | |
| 201 | 3-(HO$_2$CCH$_2$)-pipa | MS: 425 |
| 202/f | 3-(MeO$_2$CCH$_2$)-pipa | |
| 203 | 3-(HO$_2$C(CH$_2$)$_2$)-pipe | MS: 438 |
| 204/f | 3-(EtO$_2$C(CH$_2$)$_2$)-pipe | |
| 205 | 2-(H$_2$NCOCH$_2$)-mor | MS: 425 |
| 206 | 2-(HO$_2$CCH$_2$)-2,4,6,7-tetrahydro-5H-pyrazolo[4,3-c]pyridin-5-yl | MS: 462 |
| 207/f | 2-(tBuO$_2$CCH$_2$)-2,4,6,7-tetrahydro-5H-pyrazolo[4,3-c]pyridin-5-yl | MS: 518 |
| 208 | 1-(HO$_2$CCH$_2$)-1,4,6,7-tetrahydro-5H-pyrazolo[4,3-c]pyridin-5-yl | MS: 462 |
| 209/f | 1-(tBuO$_2$CCH$_2$)-1,4,6,7-tetrahydro-5H-pyrazolo[4,3-c]pyridin-5-yl | MS: 518 |
| 210 | 4-(HO$_2$CCH$_2$)-5-Me-hPy | MS: 436 |
| 211/f | 4-(EtO$_2$CCH$_2$)-5-Me-hPy | |
| 212 | (Z)-4-(carboxymethylene)-3-Me-pipe | MS: 436 |
| 213/f | (Z)-4-(ethoxycarbonylmethylene)-3-Me-pipe | |
| 214 | (E)-4-(carboxymethylene)-3-Me-pipe | MS: 436 |
| 215/f | (E)-4-(ethoxycarbonylmethylene)-3-Me-pipe | |

TABLE 18

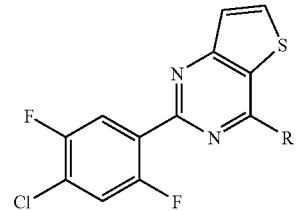

| Ex | R | Data |
|---|---|---|
| 216 | 3-(HO$_2$CCH$_2$)-4-Ms-pipa | MS: 503 |
| 217/f | 3-(EtO$_2$CCH$_2$)-4-Ms-pipa | |
| 218 | 4-Ac-3-(HO$_2$CCH$_2$)-pipa | MS: 467 |
| 219/f | 4-Ac-3-(EtO$_2$CCH$_2$)-pipa | |
| 220 | 3-(HO$_2$CCH$_2$)-4-(HOCH$_2$CO)-pipa | MS: 483 |
| 221/f | 3-(EtO$_2$CCH$_2$)-4-(HOCH$_2$CO)-pipa | |
| 222 | 4-(HO$_2$CCH$_2$)-hPy | MS: 422 |
| 223 | 4-(HO$_2$C)-hPy | MS: 408 |
| 224 | 5-(HO$_2$C)-hPy | MS: 408 |
| 225 | 3-(HO$_2$C(CH$_2$)$_2$)-pyrr | MS: 424 |
| 226 | 4-F-pipe | MS: 384 |
| 227 | 3,3-diF-pipe | MS: 402 |
| 228 | 3-Me-pipa | MS: 381 |
| 229 | trans-2,5-diMe-pipa | MS: 395 |
| 230 | cis-3,5-diMe-pipa | MS: 395 |
| 231 | 4-(3-Py-CH$_2$)-pipa | MS: 458 |
| 232 | 4-(PhO)-pipe | MS: 458 |
| 233 | 4-(HO$_2$C(CH$_2$)$_2$)-pipe | MS: 438 |
| 234/f | 4-(EtO$_2$C(CH$_2$)$_2$)-pipe | MS: 466 |
| 235 | (E)-4-(HO$_2$C—CH═CH)-pipe | MS: 436 |
| 236/f | (E)-4-(HO$_2$C—CH═CH)-pipe | MS: 464 |
| 237 | (Z)-4-(HO$_2$C—CH═CH)-pipe | MS: 436 |
| 238/f | (Z)-4-(EtO$_2$C—CH═CH)-pipe | MS: 464 |
| 239 | 3-(HO$_2$CCH$_2$)-pyrr | MS: 410 |
| 240/f | 3-(EtO$_2$CCH$_2$)-pyrr | MS: 438 |
| 241 | 4-(H$_2$NOC—CH$_2$)-pipa | MS: 424 |

TABLE 18-continued

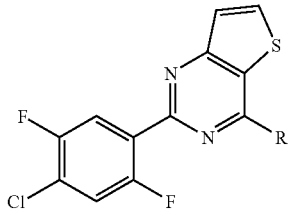

| Ex | R | Data |
|---|---|---|
| 242 | 4-(MeHNOC—CH$_2$)-pipa | MS: 438 |
| 243 | 4-(H$_2$NOC(CH$_2$)$_2$)-pipa | MS: 438 |
| 244 | 6-CO$_2$H-1,2,3,4-tetrahydroquinolin-1-yl | MS: 458 |
| 245 | 7-CO$_2$H-1,2,3,4-tetrahydroquinolin-1-yl | MS: 458 |

TABLE 19

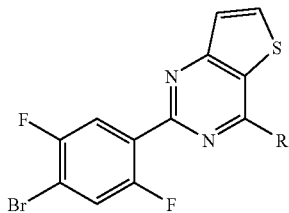

| Ex | R | Data |
|---|---|---|
| 246 | pipe | MS: 410 |
| 247 | mor | MS: 412 |
| 248 | tmor | MS: 428 |
| 249 | 4-(HO$_2$CCH$_2$)-pipe | MS: 468, 470 |
| 250/f | 4-(EtO$_2$CCH$_2$)-pipe | |
| 251 | (S)-3-(HO$_2$CCH$_2$)-pipe | MS: 468, 470 |
| 252/f | (S)-3-(EtO$_2$CCH$_2$)-pipe | |
| 253 | 4-(HO$_2$C(CH$_2$)$_2$)-pipe | MS: 482 |
| 254/f | 4-(EtO$_2$C(CH$_2$)$_2$)-pipe | MS: 510 |
| 255 | (S)-3-(HO$_2$C(CH$_2$)$_2$)-pipe | MS: 482 |
| 256/f | (S)-3-(EtO$_2$C(CH$_2$)$_2$)-pipe | MS: 510 |
| 257 | 4-(HO$_2$C(CH$_2$)$_3$)-pipe | MS: 496 |
| 258/f | 4-(EtO$_2$C(CH$_2$)$_3$)-pipe | MS: 524 |
| 259 | 4-(HO$_2$CCH$_2$)-hPy | MS: 466 |
| 260/f | 4-(EtO$_2$CCH$_2$)-hPy | MS: 494 |

TABLE 20

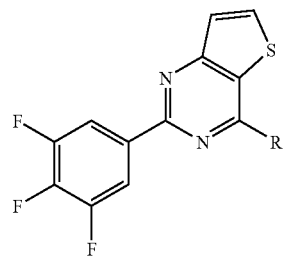

| Ex | R | Data |
|---|---|---|
| 261 | 4-(HO$_2$CCH$_2$)-pipe | MS: 408 |
| 262 | 4-(EtO$_2$CCH$_2$)-pipe | MS: 436 |
| 263/f | (S)-3-(HO$_2$CCH$_2$)-pipe | MS: 408 |
| 264/f | (S)-3-(EtO$_2$CCH$_2$)-pipe | MS: 436 |
| 265 | 4-(HO$_2$C(CH$_2$)$_2$)-pipe | MS: 422 |
| 266/f | 4-(EtO$_2$C(CH$_2$)$_2$)-pipe | |
| 267 | (S)-3-(HO$_2$C(CH$_2$)$_2$)-pipe | MS: 422 |
| 268/f | (S)-3-(EtO$_2$C(CH$_2$)$_2$)-pipe | MS: 450 |

TABLE 20-continued

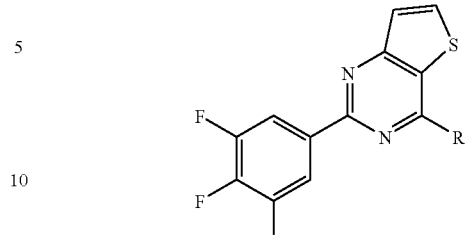

| Ex | R | Data |
|---|---|---|
| 269 | 4-(HO$_2$C(CH$_2$)$_3$)-pipe | MS: 436 |
| 270/f | 4-(EtO$_2$C(CH$_2$)$_3$)-pipe | |
| 271 | 4-(HO$_2$CCH$_2$)-hPy | MS: 406 |
| 272/f | 4-(EtO$_2$CCH$_2$)-hPy | MS: 434 |
| 273 | 3-(HO$_2$C(CH$_2$)$_2$)-pyrr | MS: 408 |
| 274/f | 3-(EtO$_2$C(CH$_2$)$_2$)-pyrr | MS: 436 |

TABLE 21

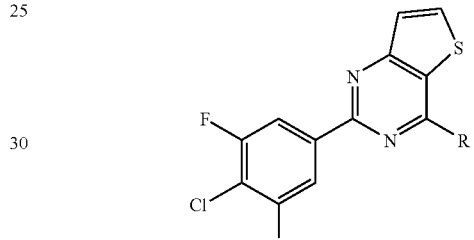

| Ex | R | Data |
|---|---|---|
| 275 | 4-(HO$_2$CCH$_2$)-pipe | MS: 424 |
| 276/f | 4-(EtO$_2$CCH$_2$)-pipe | MS: 452 |
| 277/f | 4-(HO$_2$C(CH$_2$)$_2$)-pipe | MS: 438 |
| 278/f | 4-(EtO$_2$C(CH$_2$)$_2$)-pipe | MS: 466 |
| 279 | 4-(HO$_2$C(CH$_2$)$_3$)-pipe | MS: 452 |
| 280/f | 4-(EtO$_2$C(CH$_2$)$_3$)-pipe | MS: 480 |
| 281 | (S)-3-(HO$_2$CCH$_2$)-pipe | MS: 424 |
| 282/f | (S)-3-(EtO$_2$CCH$_2$)-pipe | MS: 452 |
| 283 | (S)-3-(HO$_2$C(CH$_2$)$_2$)-pipe | MS: 438 |
| 284/f | (S)-3-(EtO$_2$C(CH$_2$)$_2$)-pipe | MS: 466 |
| 285 | 4-(HO$_2$CCH$_2$)-hPy | MS: 422 |
| 286/f | 4-(EtO$_2$CCH$_2$)-hPy | MS: 450 |

TABLE 22

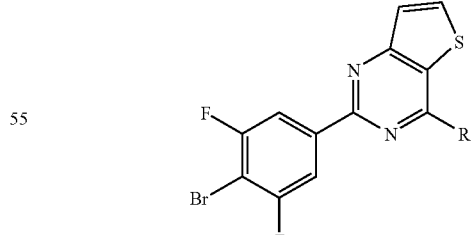

| Ex | R | Data |
|---|---|---|
| 287 | 4-(HO$_2$CCH$_2$)-pipe | MS: 468 |
| 288/f | 4-(EtO$_2$CCH$_2$)-pipe | MS: 498 |
| 289 | 4-(HO$_2$C(CH$_2$)$_2$)-pipe | MS: 496 |
| 290/f | 4-(EtO$_2$C(CH$_2$)$_2$)-pipe | MS: 524 |
| 291 | (S)-3-(HO$_2$CCH$_2$)-pipe | MS: 468 |

TABLE 22-continued

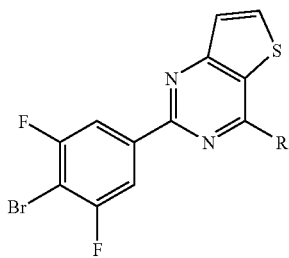

| Ex | R | Data |
|---|---|---|
| 292/f | (S)-3-(EtO$_2$CCH$_2$)-pipe | MS: 496 |
| 293 | 4-(HO$_2$CCH$_2$)-hPy | MS: 466 |
| 294/f | 4-(EtO$_2$CCH$_2$)-hPy | MS: 496 |
| 295 | 4-(HO$_2$C(CH$_2$)$_2$)-pipe | MS: 482 |
| 296/f | 4-(EtO$_2$C(CH$_2$)$_2$)-pipe | MS: 510 |
| 297 | (S)-3-(HO$_2$C(CH$_2$)$_2$)-pipe | MS: 482 |
| 298/f | (S)-3-(EtO$_2$C(CH$_2$)$_2$)-pipe | MS: 510 |

TABLE 23

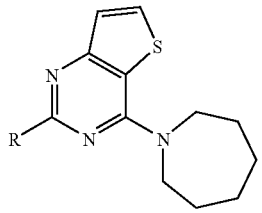

| Ex | R | Data |
|---|---|---|
| 3 | 2-(Me$_2$N)-4-Cl-5-F-Ph | MS: 405 |
| 27 | 2-(MeO)-4-Cl-5-F-Ph | MS: 392 |
| 299 | 2,4,6-triF-Ph | MS: 364 |
| 300 | 2-(HO$_2$C)-4,5-diCl-Ph | MS: 422 |
| 301 | 2-(MeO$_2$C)-4,5-diCl-Ph | MS: 436 |
| 302 | 2,5-diF-Ph | MS: 346 |
| 303 | 2,6-diF-Ph | MS: 346 |
| 304 | 3-F-4-Cl-Ph | MS: 362 |
| 305 | 2-F-4-Cl-Ph | MS: 362 |
| 306/f | 2-(HO$_2$C)-3,6-diF-4-Cl-Ph | MS: 424 |
| 307/f | 2,5-diF-3-(HO$_2$C)-4-Cl-Ph | MS: 424 |

TABLE 24

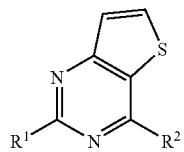

| Ex | R$^1$ | R$^2$ | Data |
|---|---|---|---|
| 308 | 2,5-diF-Ph | hPy | MS: 330 |
| 309 | 2,5-diF-Ph | 2,3,6,7-tetrahydro-1H-azepin-1-yl | MS: 344 |
| 310 | 2,5-diF-Ph | 4-(HOCH$_2$)-hPy | MS: 360 |
| 311 | 3-F-4-Cl-Ph | hPy | MS: 346 |
| 312 | 3-F-4-Cl-Ph | 2,3,6,7-tetrahydro-1H-azepin-1-yl | MS: 360 |
| 313 | 3-F-4-Cl-Ph | 4-(HOCH$_2$)-hPy | MS: 376 |

TABLE 25

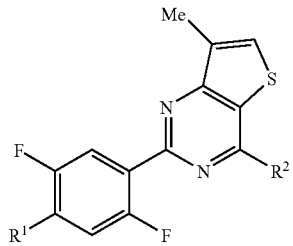

| Ex | R$^1$ | R$^2$ | Data |
|---|---|---|---|
| 314 | F | mor | MS: 366 |
| 315 | F | pipe | MS: 364 |
| 316 | F | tmor | MS: 382 |
| 317 | F | (S)-3-(HO$_2$CCH$_2$)-pipe | MS: 422 |
| 318/f | F | (S)-3-(EtO$_2$CCH$_2$)-pipe | |
| 319 | F | 4-(HO$_2$CCH$_2$)-pipe | MS: 422 |
| 320/f | F | 4-(EtO$_2$CCH$_2$)-pipe | |
| 321 | Cl | cis-3,4-diOH-pyrr | MS: 398 |
| 322 | Cl | 3-OH-azetidin-1-yl | MS: 368 |
| 323 | Cl | (S)-3-(HO$_2$CCH$_2$)-pipe | MS: 438 |
| 324/f | Cl | (S)-3-(EtO$_2$CCH$_2$)-pipe | |
| 325 | Cl | 4-(HO$_2$CCH$_2$)-pipe | MS: 438 |
| 326/f | Cl | 4-(EtO$_2$CCH$_2$)-pipe | |
| 327 | Cl | pipe | MS: 380 |
| 328/f | Cl | mor | MS: 382 |
| 329 | Cl | tmor | MS: 398 |
| 330 | Cl | cHexN(Me)- | MS: 408 |
| 331 | Br | (S)-3-(HO$_2$CCH$_2$)-pipe | MS: 482, 484 |
| 332/f | Br | (S)-3-(EtO$_2$CCH$_2$)-pipe | |
| 333 | Br | 4-(HO$_2$CCH$_2$)-pipe | MS: 482, 484 |
| 334/f | Br | 4-(EtO$_2$CCH$_2$)-pipe | |
| 335 | Br | pipe | MS: 424 |
| 336/f | Br | mor | MS: 426 |
| 337 | Br | tmor | MS: 442 |

TABLE 26

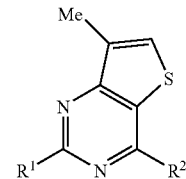

| Ex | R$^1$ | R$^2$ | Data |
|---|---|---|---|
| 2 | 2-pipe-4-Cl-5-F-Ph | pipe | MS: 445 |

TABLE 27

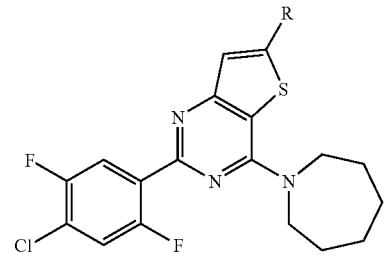

| Ex | R | Data |
|---|---|---|
| 24/f | —CO$_2$H | MS: 424 |
| 338 | —CONH$_2$ | MS: 423 |

TABLE 28

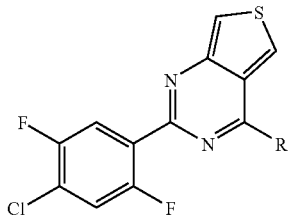

| Ex | R | Data |
|---|---|---|
| 339 | azep | MS: 380 |
| 340 | hpipa | MS: 381 |
| 341 | pipe | MS: 367 |
| 342 | 3-Me-pipa | MS: 380 |
| 343 | 4-(HO$_2$CCH$_2$)-pipe | MS: 424 |

TABLE 29

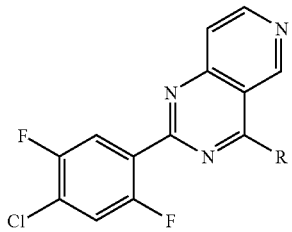

| Ex | R | Data |
|---|---|---|
| 344 | mor | MS: 363 |
| 345 | 4-HO-pipe | MS: 377 |
| 346 | pipe | MS: 361 |
| 347 | hpipa | MS: 376 |
| 348 | azep | MS: 375 |
| 349 | pipa | ES-MS: 362 |
| 350 | 4-(HOCH$_2$CH(OH))-pipe | ES-MS: 421 |
| 351 | 3-Me-pipe | ES-MS: 375 |
| 352 | 4-(HOCH$_2$)$_2$CH)-pipe | MS: 435 |
| 353 | 4-(HO(CH$_2$)$_2$O)-pipe | ES-MS: 421 |
| 354/f | 4-Boc-pipa | MS: 462 |
| 355 | 4-(EtO$_2$CCH$_2$)-pipe | ES-MS: 447 |
| 356 | hPy | ES-MS: 359 |

TABLE 30

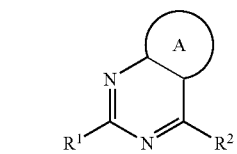

| Ex | R$^1$ | | R$^2$ | Data |
|---|---|---|---|---|
| 357 | 2,5-diF-4-Cl-Ph | (2,3-dimethylpyridinyl) | mor | MS: 363 |

TABLE 30-continued

| Ex | R$^1$ | | R$^2$ | Data |
|---|---|---|---|---|
| 358 | 2,5-diF-4-Cl-Ph | (2,3-dimethylpyridinyl) | pipe | MS: 361 |
| 359 | 2,5-diF-4-Cl-Ph | (2,3-dimethylpyridinyl) | 4-HO-pipe | MS: 377 |
| 360 | 2,5-diF-4-Cl-Ph | (3,4-dimethylpyridinyl) | mor | ES-MS: 363 |
| 361 | 2,5-diF-4-Cl-Ph | (dimethylthiazolyl) | azep | MS: 381 |
| 362 | 2,5-diF-4-Cl-Ph | (dimethylthiazolyl) | 4-(HO(CH$_2$)$_2$)-pipa | MS: 412 |

NMR data of compounds in some Examples are given in Tables 31 to 32 below. Symbols in Tables represent following meaning. NMR: NMR data (δ(ppm)) of peaks in $^1$H-NMR measured using tetramethylsilane as an internal standard and DMSO-d$_6$ as a solvent unless specifically noted).

TABLE 31

| Ex | Data |
|---|---|
| 5 | NMR: 1.33-1.50(1H, m), 1.52-1.70(1H, m), 1.80-1.95(2H, m), 1.98-2.20(1H, m), 2.20-2.40(2H, m), 3.29(1H, dd), 3.43(1H, dd), 4.62(1H, d), 4.69(1H, dd) 7.62(1H, dd), 7.86(1H, dd), 8.10(1H, dd), 8.44(1H, dd). |
| 25 | NMR: 1.39(2H, dq), 1.86-2.04(2H, m), 2.04-2.20(1H, m), 2.58(2H, d), 3.36(2H, dd), 4.83(2H, d), 7.61(1H, d), 7.86(1H, dd), 8.09(1H, dd), 8.43(1H, d). |
| 32 | NMR: 1.20-1.45(2H, m), 1.92(2H, d), 2.00-2.30(3H, m), 3.25-3.50(2H, m), 4.80(2H, d), 7.50-7.65(1H, m), 7.70-7.85(1H, m), 8.05-8.25(1H, m), 8.30-8.50(1H, m). |
| 34 | NMR: 1.35-1.55(1H, m), 1.55-1.75(1H, m), 1.80-2.00(2H, m), 2.00-2.20(1H, m), 2.20-2.40(2H, m), 3.36(1H, dd), 3.49 (1H, dd), 4.50-4.85(2H, m), 7.71(1H, d), 7.82(1H, dt), 8.10-8.30(1H, m), 8.53(1H, d). |

TABLE 31-continued

| Ex | Data |
|---|---|
| 38 | NMR: 1.30-1.42(1H, m), 1.46-1.74(4H, m), 1.80-1.95(2H, m), 2.34(2H, t), 3.17-3.28(1H, m), 3.43(1H, t), 4.60-4.73 (2H, m), 7.67(1H, d), 7.75-7.85(1H, m), 8.13-8.22(1H, m), 8.43(1H, d). |
| 42 | NMR: 1.50-1.90(3H, m), 2.00-2.50(4H, m), 3.30-4.50(4H, m), 7.68(1H, d), 7.80-7.88(1H, m), 8.14-8.24(1H, m), 8.55(1H, d). |
| 44 | NMR: 2.34-2.41(2H, m), 3.08(2H, s), 4.16(2H, t), 4.57-4.62 (2H, m), 7.64(1H, d), 7.75-7.85(1H, m), 8.14-8.22(1H, m), 8.49 (1H, d). |
| 61 | NMR: 1.35-1.48(1H, m), 1.54-1.68(1H, m), 1.80-1.94(2H, m), 2.00-2.12(1H, m), 2.22-2.34(2H, m), 3.22-3.31(1H, m), 3.36-3.46(1H, m), 4.58-4.72(2H, m), 7.57-7.61(1H, m), 7.84(1H, dd), 8.09(1H, dd), 8.39-8.42(1H, m). |
| 135 | NMR: 1.20-1.45(2H, m), 1.80-2.00(2H, m), 2.00-2.25(3H, m), 3.40(2H, dd), 4.79(2H, d), 7.65(1H, d), 7.89(1H, dd), 8.11(1H, dd), 8.47(1H, d). |
| 158 | NMR: 2.70-5.50(10H, m), 7.63(1H, d), 7.81(1H, dd), 8.13 (1H, dd), 8.44(1H, d). |
| 184 | NMR: 1.55-1.80(2H, m), 1.80-1.95(2H, m), 3.05-3.28(3H, m), 3.30-3.65(7H, m), 4.70-4.90(2H, m), 7.61(1H, d), 7.85(1H, dd), 8.09(1H, dd), 8.42(1H, d). |
| 187 | NMR: 2.55(2H, t), 3.60-3.84(6H, m), 4.00-4.20(4H, m), 7.61 (1H, d), 7.84(1H, dd), 8.11(1H, dd), 8.43(1H, dd). |
| 188 | NMR: 3.45-3.62(4H, m), 3.64-4.00(4H, m), 4.00-4.25(4H, m), 4.42(1H, t), 7.62(1H, dd), 7.85(1H, dd), 8.12(1H, dd), 8.44 (1H, dd). |
| 191 | NMR: 1.80-2.00(2H, m), 2.00-2.20(2H, m), 3.22-3.35(1H, m), 3.75-3.95(2H, m), 4.20-4.45(2H, m), 7.61(1H, d), 7.83(1H, dd), 8.09(1H, dd), 8.41(1H, d). |
| 210 | NMR: 1.74(3H, s), 2.30-2.40(2H, m), 3.09(2H, s), 4.11(2H, t), 4.46(2H, s), 7.62(1H, d), 7.87(1H, dd), 8.11(1H, dd), 8.45 (1H, d). |
| 212 | NMR: 1.08(3H, d), 2.53-2.65(1H, m), 3.00-3.15(2H, m), 3.83 (1H, dd), 4.25(1H, dd), 4.41(1H, d), 4.68(1H, d), 5.69(1H, s), 7.57(1H, d), 7.83(1H, dd), 8.09(1H, d), 8.40(1H, d). |
| 214 | NMR: 1.08(3H, d), 2.54-2.67(1H, m), 3.00-3.20(2H, m), 3.85 (1H, dd), 4.27(1H, dd), 4.43(1H, d), 4.70(1H, d), 5.69(1H, s), 7.61(1H, d), 7.86(1H, dd), 8.11(1H, dd), 8.43(1H, d). |
| 222 | NMR: 2.30-2.44(2H, m), 3.08(2H, s), 4.08-4.22(2H, m), 4.53-4.65(2H, m), 5.73(1H, br), 7.65(1H, d), 7.88(1H, dd), 8.13(1H, dd), 8.49(1H, d). |
| 225 | NMR(80° C.): 1.64-1.84(3H, m), 2.16-2.27(1H, m), 2.27-2.42(3H, m), 3.44-3.58(1H, m), 3.78-3.94(1H, m), 4.02-4.24(2H, m), 7.57(1H, d), 7.74(1H, dd), 8.07(1H, dd), 8.37(1H, d). |

TABLE 32

| Ex | Data |
|---|---|
| 233 | NMR: 1.19-1.30(2H, m), 1.46-1.52(2H, m), 1.65-1.75(1H, m), 1.87-1.93(2H, m), 2.27(2H, t), 3.29-3.36(2H, m), 4.77-4.83 (2H, m), 7.61(1H, d), 7.87(1H, dd), 8.09(1H, dd), 8.43(1H, d) |
| 255 | NMR: 1.30-1.40(1H, m), 1.47-1.70(4H, m), 1.80-1.92(2H, m), 2.34(2H, t), 3.18(1H, t), 3.39(1H, t), 4.65(2H, t), 7.60(1H, d), 7.94(1H, dd), 8.04(1H, dd), 8.41(1H, d). |
| 259 | NMR: 2.36(2H, s), 3.07(2H, s), 4.13(2H, t), 4.56(2H, s), 5.73(1H, s), 7.59(1H, d), 7.93(1H, dd), 8.05(1H, dd), 8.42 (1H, d). |
| 273 | NMR: 1.60-1.90(3H, m), 2.10-2.50(4H, m), 3.40-4.00(2H, m), 4.00-4.20(2H, m), 7.70(1H, d), 8.36(2H, t), 8.50(1H, d). |
| 302 | NMR: 1.57(4H, brs), 1.90(4H, brs), 4.08(4H, dd), 7.48-7.54 (2H, m), 7.61-7.66(1H, br), 7.85-7.87(1H, br), 8.48-8.52 (1H, br). |
| 304 | NMR: 1.57(4H, brs), 1.91(4H, brs), 4.10(4H, dd), 7.74(1H, d), 7.82(1H, dd), 8.29(1H, dd), 8.41(1H, d), 8.47(1H, d). |
| 308 | NMR: 2.36-2.38(2H, br), 4.16-4.18(2H, m), 4.60-4.62(2H, m), 5.87-5.90(1H, m), 5.97-6.01(1H, m), 7.47-7.56(2H, m), 7.67 (1H, d), 7.82-7.92(1H, m), 8.51(1H, d). |
| 309 | NMR: 2.54(4h, brs), 4.18-4.20(4H, m), 5.70-5.77(2H, m), 7.47-7.56(2H, m), 7.65(1H, d), 7.84-7.88(1H, m), 8.51(1H, d). |
| 310 | NMR: 2.29(2H, brs), 3.91(2H, brs), 4.15-4.18(2H, m), 4.60 (2H, brs), 5.77(1H, brs), 7.45-7.53(2H, m), 7.62(1H, d), 7.85-7.89(1H, m), 8.47(1H, d). |

TABLE 32-continued

| Ex | Data |
|---|---|
| 311 | NMR: 2.37-2.39(2H, brs), 4.16-4.19(2H, brs), 4.60-4.61(2H, brs), 7.74(1H, d), 7.82(1H, dd), 8.29(1H, dd), 8.41(1H, d), 8.47(1H, d). |
| 312 | NMR: 2.56(4H, brs), 4.19-4.22(4H, m), 5.74(2H, dd), 7.73(1H, d), 7.80(1H, dd), 8.28(1H, dd), 8.39(1H, dd), 8.47(1H, d). |
| 313 | NMR: 2.31(2H, brs), 3.92(2H, brs), 4.17-4.20(2H, m), 4.61 (2H, brs), 5.79(1H, brs), 7.66-7.68(1H, m), 7.79(1H, dd), 8.29(1H, d), 8.37-8.43(2H, m). |
| 319 | NMR: 1.20-1.40(2H, m), 1.80-2.00(2H, m), 2.00-2.17(1H, m), 2.21(2H, d), 2.42(3H, s), 3.20-3.40(2H, m), 4.65-4.85(2H, m), 7.70(1H, dt), 8.00(1H, s), 8.05-8.20(1H, m). |
| 325 | NMR: 1.20-1.30(2H, m), 1.75-1.95(2H, m), 2.00-2.16(1H, m), 2.20(2H, d), 2.41(3H, s), 3.15-3.40(2H, m), 4.65-4.85(2H, m), 7.78(1H, dd), 7.99(1H, s), 8.06(1H, dd). |
| 333 | NMR: 1.20-1.40(2H, m), 1.75-1.95(2H, m), 2.00-2.17(1H, m), 2.21(2H, d), 2.41(3H, s), 3.20-3.40(2H, m), 4.65-4.85(2H, m), 7.87(1H, dd), 7.90-8.10(2H, m). |
| 345 | NMR: 1.59-1.67(2H, m), 1.91-1.99(2H, m), 3.86-3.95(3H, m), 4.32-4.38(2H, m), 7.84-7.88(1H, m), 7.90(1H, d), 8.14-8.19 (1H, m), 8.77(1H, d), 9.47(1H, s) |

Chemical structures of other compounds of the present invention are given in Tables 33 to 35 below. These compounds are readily prepared using the above preparation methods, methods described in Examples, methods obvious to those skilled in the art, or modified methods thereof. Symbols in Tables represent the following meaning.

No: Compound number

TABLE 33

| No | Structure |
|---|---|
| A1 | (structure) |
| A2 | (structure) |
| A3 | (structure) |

TABLE 33-continued

| No | Structure |
|---|---|
| A4 | |
| A5 | |
| A6 | |
| A7 | |
| A8 | |
| A9 | 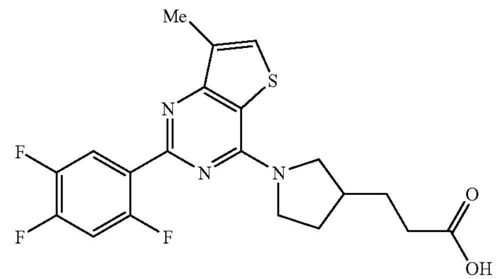 |
| A10 | 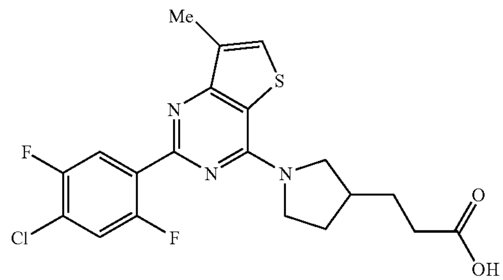 |
| A11 | 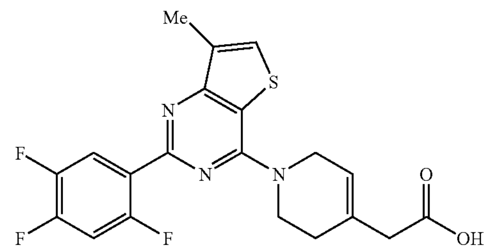 |
| A12 | 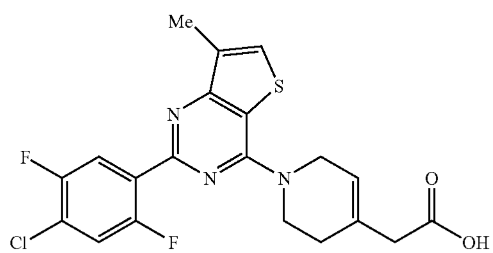 |
| A13 | 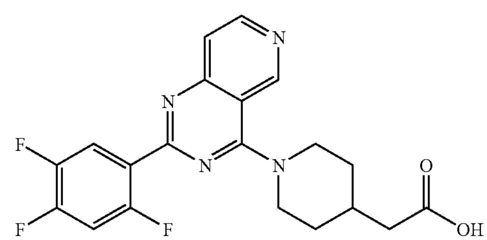 |
| A14 | 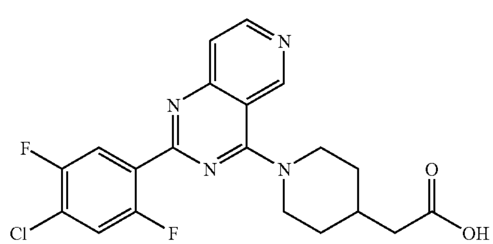 |

TABLE 34
| No | Structure |
|----|-----------|
| A15 | 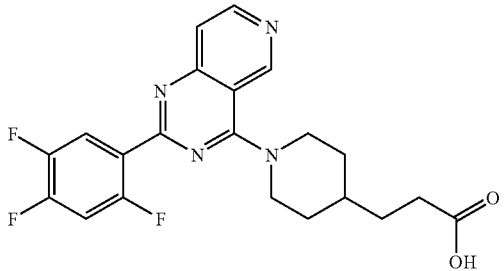 |
| A16 | 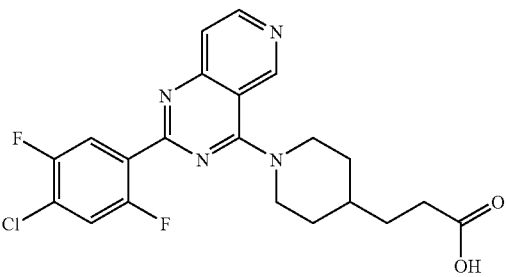 |
| A17 | 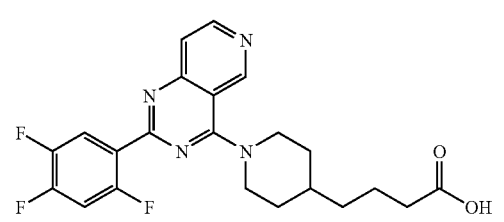 |
| A18 | 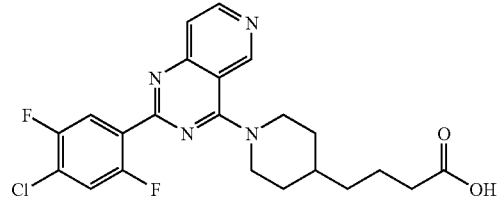 |
| A19 | 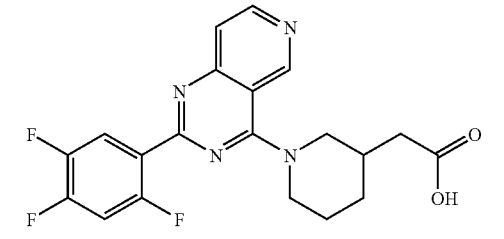 |
| A20 | 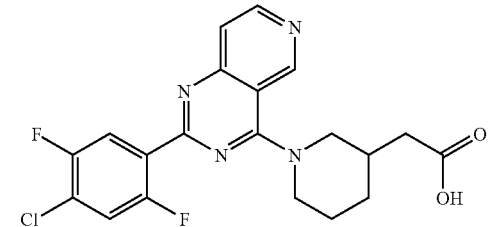 |
TABLE 34-continued
| No | Structure |
|----|-----------|
| A21 | 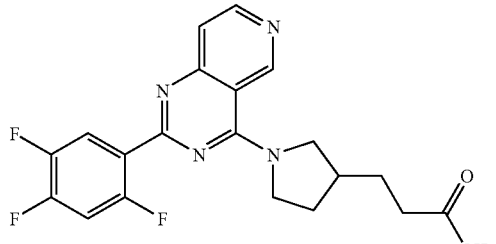 |
| A22 | 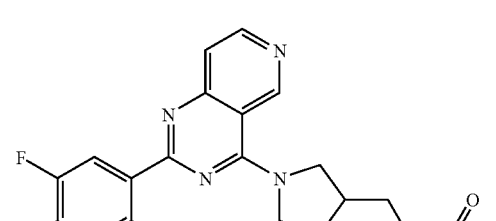 |
| A23 | 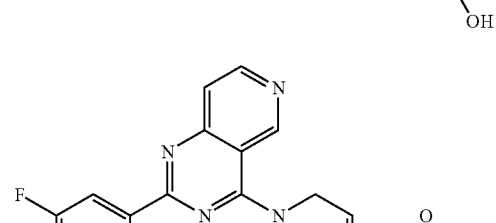 |
| A24 | 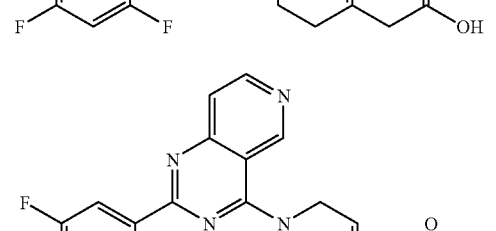 |
| A25 | 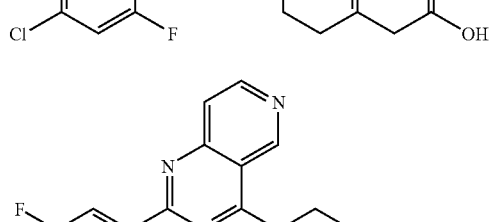 |
| A26 | 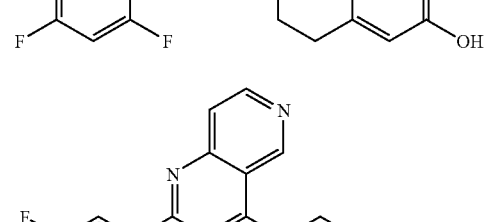 |

TABLE 34-continued

| No | Structure |
|---|---|
| A27 | 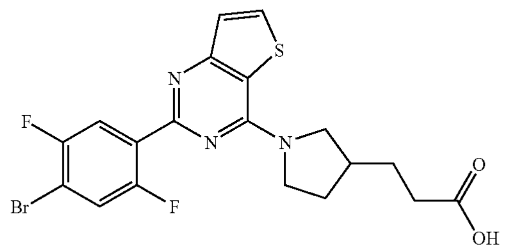 |
| A28 | 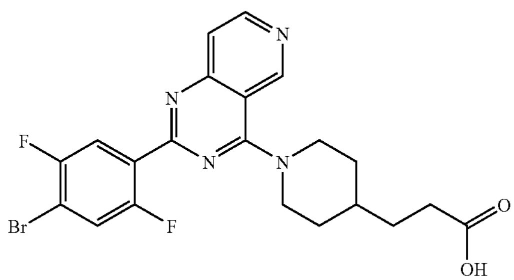 |

TABLE 35

| No | Structure |
|---|---|
| A29 | 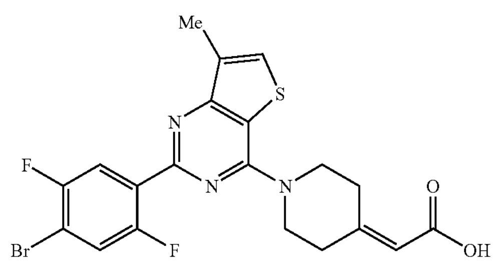 |
| A30 | 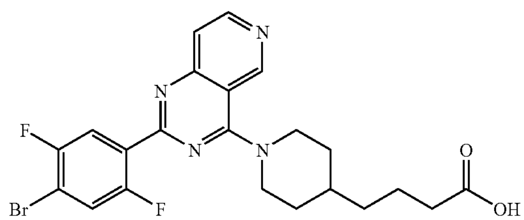 |
| A31 | 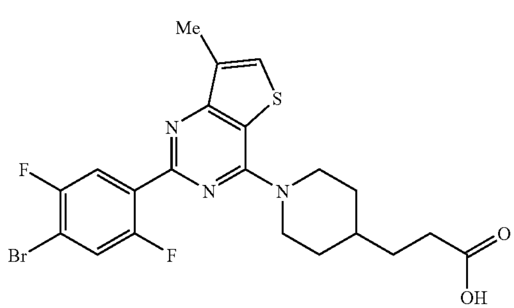 |

TABLE 35-continued

| No | Structure |
|---|---|
| A32 | 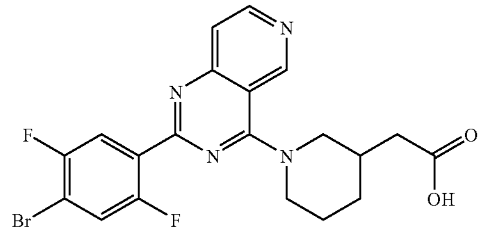 |
| A33 | 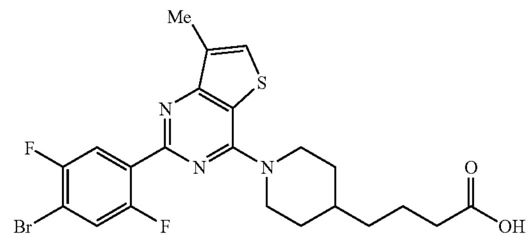 |
| A34 | 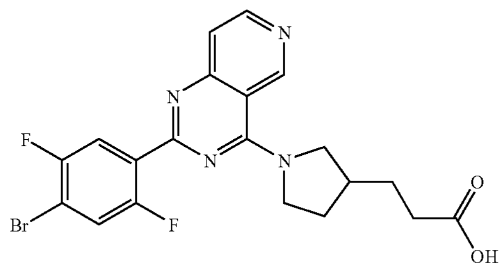 |
| A35 | 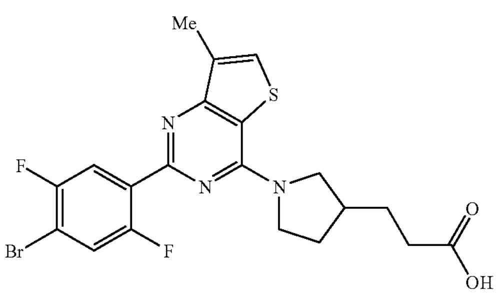 |
| A36 | 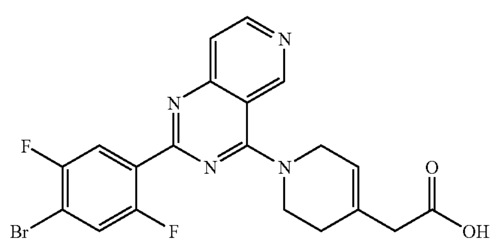 |
| A37 | 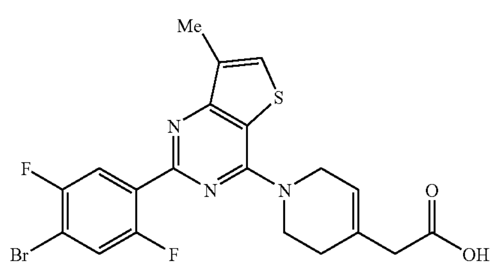 |

TABLE 35-continued

| No | Structure |
|---|---|
| A38 | 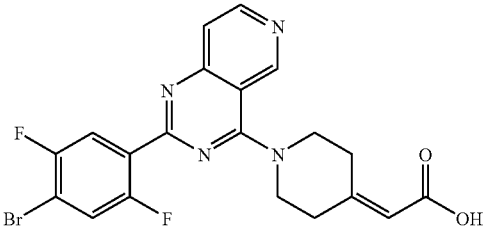 |
| A39 | 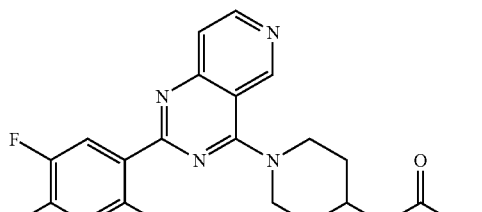 |

INDUSTRIAL APPLICABILITY

The compounds of the present invention exhibit excellent promoting activity on insulin secretion and preventive activity against hyperglycemia. Hence, the compounds of the present invention, based on these actions, are useful for treating and/or preventing insulin-dependent diabetes (type 1 diabetes), non-insulin-dependent diabetes (type 2 diabetes), insulin-resistant diseases, obesity, and the like.

The invention claimed is:

1. A method of inhibiting hyperglycemia comprising administering to a subject in need thereof an effective amount of the pharmaceutical composition comprising
a fused pyrimidine compound represented by Formula (I) or a pharmaceutically acceptable salt thereof:

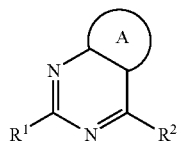

(I)

wherein A is selected from the group consisting of

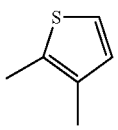 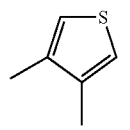 and 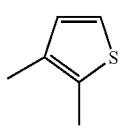

wherein the carbon atoms which form the structure A may be substituted with one or more group(s) selected from the group consisting of lower alkyl, —O-lower alkyl, halogen, carboxyl, —CO$_2$-lower alkyl and carbamoyl;
—R$^1$ is a phenyl substituted with at least one halogen; and
—R$^2$ is an optionally substituted cycloamino,
and a pharmaceutically acceptable carrier or excipient.

2. The method according to claim 1, wherein A is

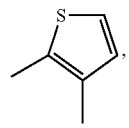

wherein the carbon atoms which form the structure A may be substituted with one or more group(s) selected from the group consisting of lower alkyl, —O-lower alkyl, halogen, carboxyl, —CO$_2$-lower alkyl and carbamoyl.

3. The method according to claim 1, wherein R$^1$ is phenyl substituted with at least three halogens.

4. The method according to claim 3, wherein R$^2$ is optionally substituted piperazino.

5. The method according to claim 3, wherein R$^2$ is optionally substituted piperidino.

6. The method according to claim 1, wherein A is

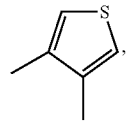

wherein the carbon atoms which form the structure A may be substituted with one or more group(s) selected from the group consisting of lower alkyl, —O-lower alkyl, halogen, carboxyl, —CO$_2$-lower alkyl and carbamoyl.

7. The method according to claim 6, wherein R$^1$ is phenyl substituted with at least three halogens.

8. The method according to claim 7, wherein R$^2$ is optionally substituted piperazino.

9. The method according to claim 7, wherein R$^2$ is optionally substituted piperidino.

10. The method according to claim 1, wherein A is

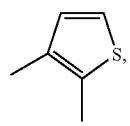

wherein the carbon atoms which form the structure A may be substituted with one or more group(s) selected from the group consisting of lower alkyl, —O-lower alkyl, halogen, carboxyl, —CO$_2$-lower alkyl and carbamoyl.

11. The method according to claim 10, wherein R$^1$ is phenyl substituted with at least three halogens.

12. The method according to claim 11, wherein R$^2$ is optionally substituted piperazino.

13. The method according to claim 11, wherein R$^2$ is optionally substituted piperidino.

14. The method of claim 1, wherein said administering is oral.

15. The method of claim 1, wherein said administering is parenteral.

16. The compound according to claim 10, wherein R$^1$ is phenyl substituted with at least three halogens.

17. The compound according to claim 16, wherein R$^2$ is optionally substituted piperazino.

18. The compound according to claim 16, wherein R$^2$ is optionally substituted piperidino.

19. A fused pyrimidine compound represented by Formula (I) or a pharmaceutically acceptable salt thereof:

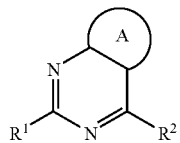
(I)

wherein A is

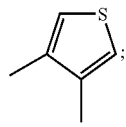

wherein the carbon atoms which form the structure A may be substituted with one or more group(s) selected from the group consisting of lower alkyl, —O-lower alkyl, halogen, carboxyl, —CO$_2$-lower alkyl and carbamoyl;
—R$^1$ is a phenyl substituted with at least three halogens; and
—R$^2$ is an optionally substituted cycloamino.

20. The compound according to claim 19, wherein R$^2$ is optionally substituted piperazino.

21. The compound according to claim 19, wherein R$^2$ is optionally substituted piperidino.

22. A fused pyrimidine compound represented by Formula (I) or a pharmaceutically acceptable salt thereof:

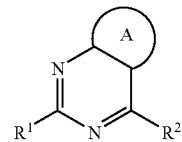
(I)

wherein A is

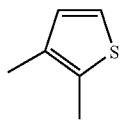

wherein the carbon atoms which form the structure A may be substituted with one or more group(s) selected from the group consisting of lower alkyl, —O-lower alkyl, halogen, carboxyl, —CO$_2$-lower alkyl and carbamoyl;
—R$^1$ is a phenyl substituted with at least one halogen; and
—R$^2$ is an optionally substituted cycloamino.

* * * * *